United States Patent
Mazlish et al.

(10) Patent No.: US 10,275,573 B2
(45) Date of Patent: Apr. 30, 2019

(54) USER INTERFACE FOR DIABETES MANAGEMENT SYSTEM

(71) Applicant: Bigfoot Biomedical, Inc., Milpitas, CA (US)

(72) Inventors: Bryan Mazlish, Palo Alto, CA (US); Jeffrey Brewer, Palo Alto, CA (US); Lane Desborough, Thousand Oaks, CA (US); Jennifer Block, Menlo Park, CA (US); Robert Weishar, Daly City, CA (US); Alan Schachtely, Dublin, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 181 days.

(21) Appl. No.: 15/402,493

(22) Filed: Jan. 10, 2017

(65) Prior Publication Data

US 2017/0199985 A1 Jul. 13, 2017

Related U.S. Application Data

(60) Provisional application No. 62/278,231, filed on Jan. 13, 2016.

(51) Int. Cl.
*G06F 19/00* (2018.01)
*G16H 20/60* (2018.01)
(Continued)

(52) U.S. Cl.
CPC ....... *G06F 19/3468* (2013.01); *A61M 5/1723* (2013.01); *G06F 19/00* (2013.01);
(Continued)

(58) Field of Classification Search
CPC . G16H 20/17; G16H 20/60; A61M 2205/583; A61M 2230/201; A61M 5/1723
See application file for complete search history.

(56) References Cited

U.S. PATENT DOCUMENTS 8,417,312 B2 * 4/2013 Kamath ............. A61B 5/14532
600/347
2006/0272652 A1 12/2006 Stocker et al.
(Continued)

FOREIGN PATENT DOCUMENTS

WO WO 2008/048584 4/2008
WO WO 2013/097929 7/2013

OTHER PUBLICATIONS

International Search Report and Written Opinion in Application No. PCTUS/2017/012806, dated Apr. 5, 2017, 14 pages.
(Continued)

*Primary Examiner* — Bradley J Osinski
(74) *Attorney, Agent, or Firm* — Fish & Richardson P.C.

(57) ABSTRACT

A diabetes management system including a pump for dispensing a medicant and a control device for controlling the pump includes a user interface for controlling functions of the pump and providing information related to operation of the pump and other information. The user interface can display blood glucose information and insulin dosing data such that a user can appropriately act on the information and/or gain confidence that the diabetes management system is operating appropriately to manage the disease. User interfaces provided herein can include displays of current and projected glucose values, bolus calculators, charts displaying glucose levels and/or insulin delivery data, system maintenance reminders, system status information, patient configuration input screens, and log-in screens. Diabetes management systems can include insulin pumps, continuous glucose monitors, blood glucose monitors, mobile computing devices, servers, and/or other insulin delivery devices (e.g., insulin pens).

20 Claims, 15 Drawing Sheets

(51) Int. Cl.
*G16H 20/17* (2018.01)
*A61M 5/172* (2006.01)
*G16H 40/63* (2018.01)

(52) U.S. Cl.
CPC ......... *G06F 19/3418* (2013.01); *G16H 20/17* (2018.01); *G16H 20/60* (2018.01); *G16H 40/63* (2018.01); *A61M 2205/18* (2013.01); *A61M 2205/3569* (2013.01); *A61M 2205/3584* (2013.01); *A61M 2205/502* (2013.01); *A61M 2205/581* (2013.01); *A61M 2205/582* (2013.01); *A61M 2205/583* (2013.01); *A61M 2230/201* (2013.01)

(56) References Cited

U.S. PATENT DOCUMENTS

| 2013/0172710 A1* | 7/2013 | Mears | G06F 19/3468 |
| | | | 600/365 |
| 2014/0128705 A1* | 5/2014 | Mazlish | A61B 5/4866 |
| | | | 600/365 |

OTHER PUBLICATIONS

Percival et al., "Closed-Loop Control and Advisory Mode Evaluation of an Artificial Pancreatic β Cell: Use of Proportional—Integral—Derivative Equivalent Model-Based Controllers," J Diabetes Sci Tech 2(4):636-644, Jul. 2008.
International Preliminary Report on Patentability in Application No. PCTUS/2017/012806, dated Jul. 26, 2018, 9 pages.

* cited by examiner

Insulin Delivery System

Insulin Pump Details

Controller Details

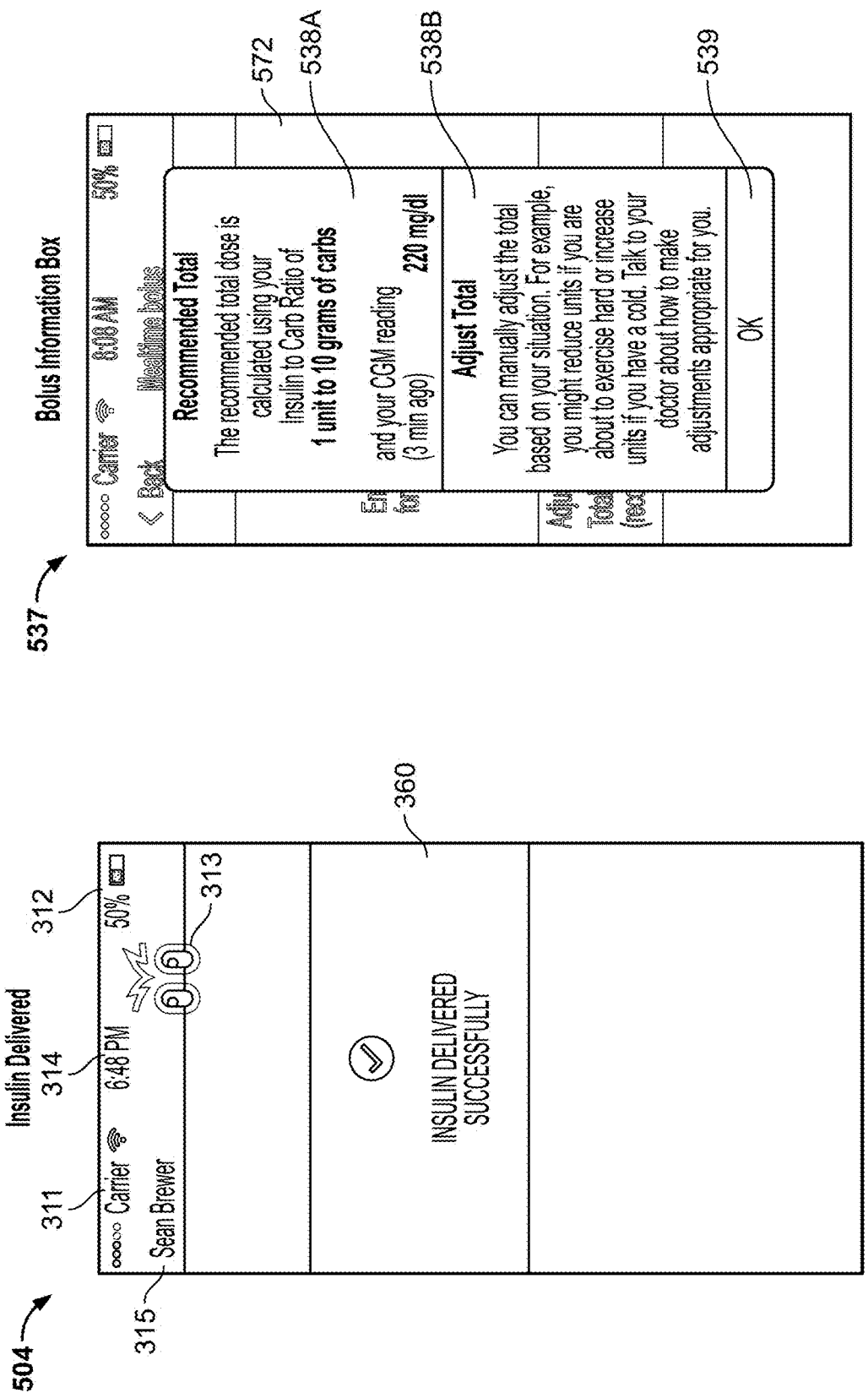

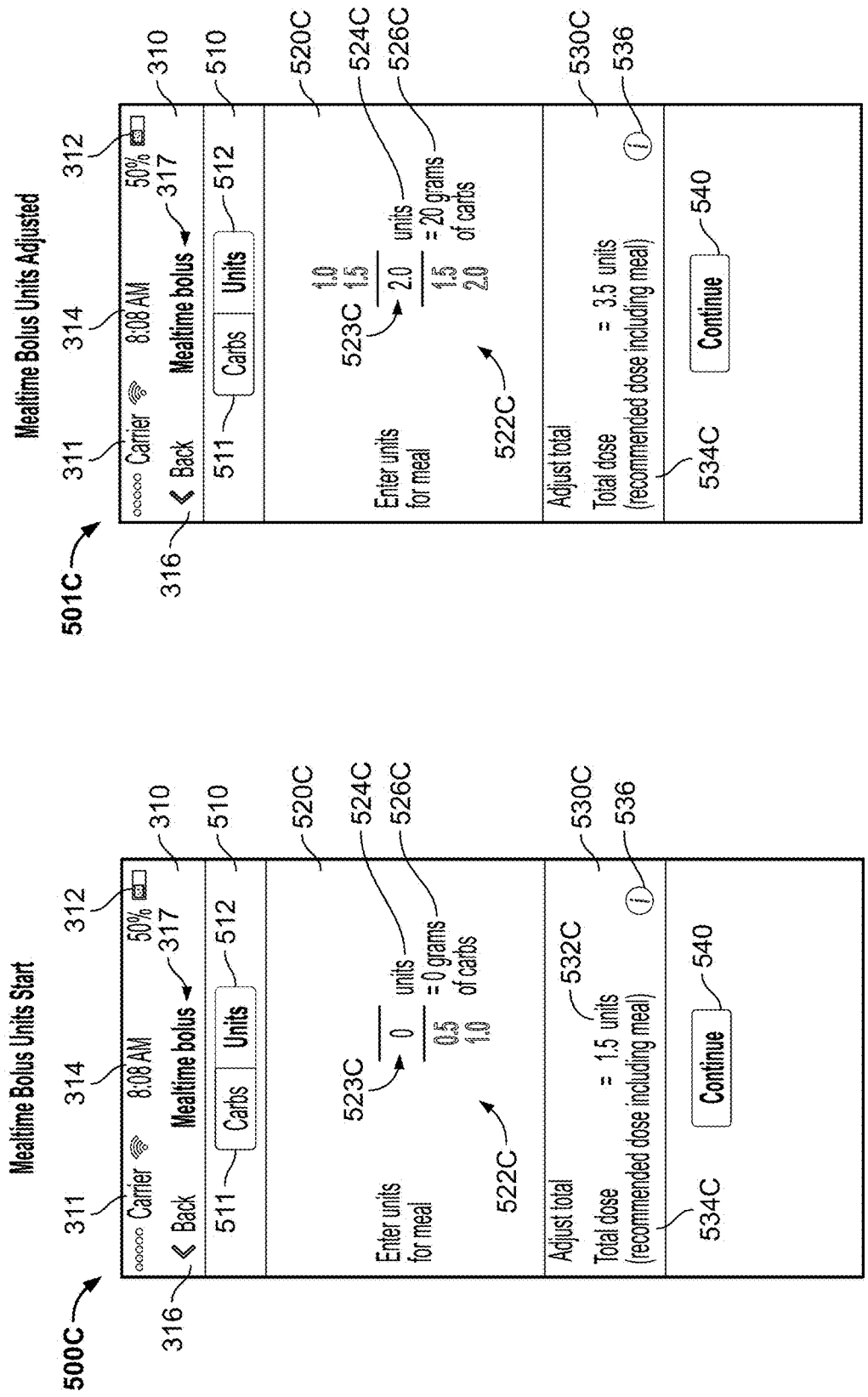

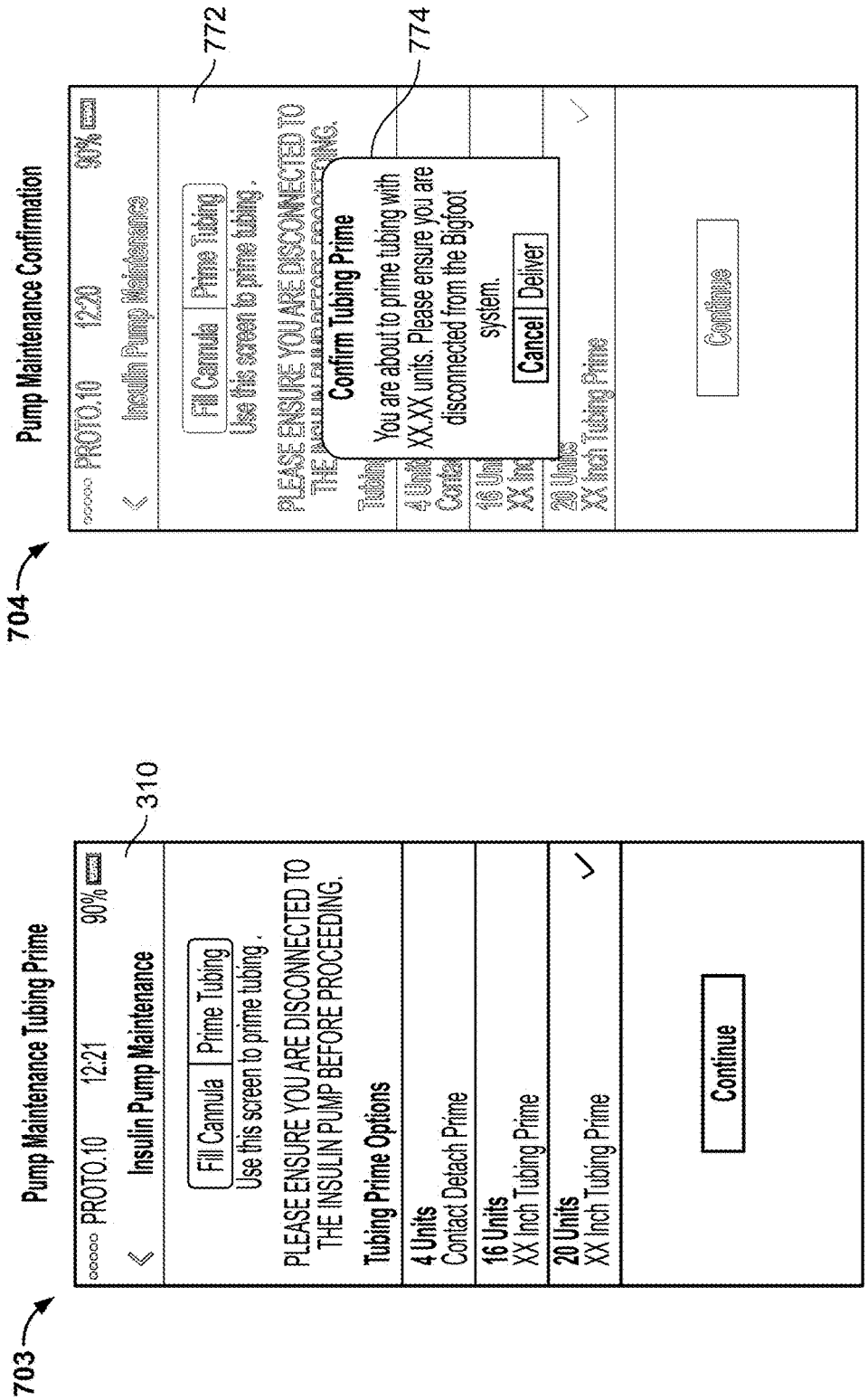

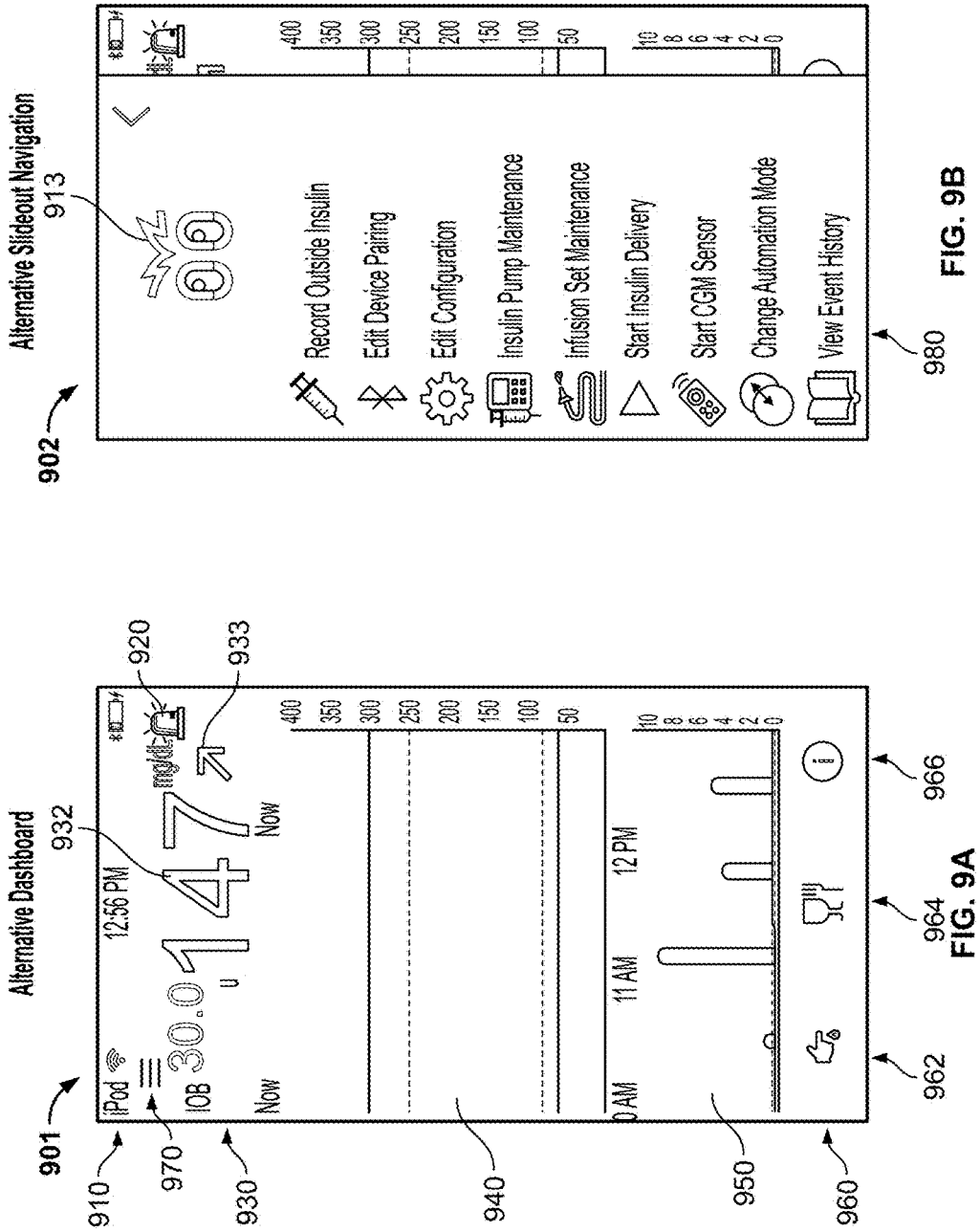

USER INTERFACE FOR DIABETES MANAGEMENT SYSTEM

CROSS-REFERENCE TO RELATED APPLICATIONS

This application claims priority to U.S. Application Ser. No. 62/278,231, filed on Jan. 13, 2016.

TECHNICAL FIELD

This document relates a diabetes management system including a pump for dispensing a medicant and a control device for controlling the pump, the control device having a user interface for controlling functions of the pump and providing information related to operation of the pump and other information. For example, the control device can be a mobile computing device in wireless communication with one or more glucose sensors and/or insulin delivery devices and the user interface can be an application running on the mobile computing device.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e. the presence of an excessive amount of analyte within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood analyte within normal limits. Such glycemic control is achieved by regularly supplying external drugs to the body of the patient to thereby reduce the elevated levels of blood analyte.

Conventionally, an external biologically effective drug (e.g., insulin or its analog) is commonly administered by means of multiple, daily injections of a mixture of rapid and intermediate acting drug via a hypodermic syringe. While this treatment does not require the frequent estimation of blood analyte, it has been found that the degree of glycemic control achievable in this way is suboptimal because the delivery is unlike physiological hormone production, according to which, hormones enter the bloodstream at a lower rate and over a more extended period of time.

Improved glycemic control may be achieved by the so-called intensive drug therapy which is based on multiple daily injections, including one or two injections per day of a long acting drug for providing a basal level of drug and additional injections of a rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of other drug delivery devices, such as insulin pumps, relieving the patient of the need for syringes or drug pens and the administration of multiple, daily injections. Insulin pumps allow for the delivery of insulin in a manner that bears greater similarity to the naturally occurring physiological processes and can be controlled to follow standard or individually modified protocols to give the patient better glycemic control. In some circumstances, an insulin pump device can store (via input from a clinician or a user) a number of settings (e.g., dosage parameters or other settings) that are customized by the physician for the particular user. In one example, an infusion pump device can be programmed to store a user's insulin sensitivity (e.g., in units of mg/dL/insulin unit), which can be employed by the infusion pump system when calculating a correction bolus dosage for that particular user. In another example, an infusion pump device can be programmed to store a user's carbohydrate ratio (e.g., in units of g/insulin unit), which can be employed by the infusion pump system when calculating meal bolus dosage for that particular user. In many cases, these user-specific settings are manually input into the infusion pump device via user interface buttons on the infusion pump device. If any of these settings are erroneously input into the infusion pump system (e.g., due to a transcribing error or other error when manually inputting the data), the resulting consequences could lead to improper bolus dosage calculations resulting in blood glucose levels that are unnecessarily too high or too low.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing drug or a suitable biologically effective material into the diabetic patient at a basal rate with additional drug or "bolus" to account for meals or high analyte values, levels, or concentrations. The drug delivery device typically is connected to an infuser, better known as an infusion set, by a flexible hose. The infuser typically has a subcutaneous cannula, and an adhesive backed mount on which the cannula is attached. The cannula may include a quick disconnect to allow the cannula and mount to remain in place on the skin surface of the user while the flexible tubing is disconnected from the infuser. Regardless of the type of drug delivery device, blood analyte monitoring is typically required to achieve acceptable glycemic control. For example, delivery of suitable amounts of drug by the drug delivery device requires that the patient frequently determine his or her blood analyte level and manually input this value into a user interface for the external drug delivery device, which then may calculate a suitable modification to the default or currently in-use drug delivery protocol, i.e., dosage and timing, and subsequently communicates with the drug delivery device to adjust its operation accordingly. The determination of blood analyte concentration is typically performed by means of an episodic measuring device such as a hand-held electronic meter, which receives blood samples via enzyme-based test strips and calculates the blood analyte value based on the enzymatic reaction. In recent years, continuous analyte monitoring has also been utilized with drug delivery devices to allow for greater control of the drug(s) being infused into the diabetic patients.

People with diabetes and their health care provider (HCP) bear a great deal of cognitive burden in managing intensive drug therapy. Delivering the correct amount of the drug at the correct time is an extremely challenging endeavor. It requires the patient to make dosing determinations multiple times per day and it requires a combination of the patient and the HCP to re-calibrate the therapeutic parameters of the therapy on an episodic time frame that varies from individual to individual.

In light of the many deficiencies and problems associated with current systems and methods for maintaining proper glycemic control, enormous resources have been put into finding better solutions. Developing workable solutions to the problem that are simple, safe, reliable and able to gain regulatory approval has, however, proved to be elusive. For years, researchers have contemplated coupling a continuous glucose monitoring system with an insulin delivery device to provide an "artificial pancreas" to assist people living with diabetes. Their efforts have yet to result in a commercial product. What has been needed is a system and method that provides a level of automatic control of drug delivery devices for improved drug delivery and glycemic control that is simple, safe, and reliable in a real world setting.

SUMMARY

User interfaces provided herein can simplify the management of diabetes, reduce the cognitive burden on users, and reassure the user that the diabetes management system is acting appropriately to manage the disease. User interfaces provided herein can be designed to highlight actionable information so that an ordinary user can quickly determine an appropriate corrective action. In some cases, user interfaces provided herein can be used to deliver mealtime boluses and/or input therapeutically relevant information. In some cases, user interfaces provided herein can display blood glucose data and project future blood glucose values. In some cases, user interfaces provided herein can display medication delivery information. In some cases, user interfaces provided herein can inform a user about upcoming predicted system maintenance activities and detected problems with the system that require maintenance.

In general, one innovative aspect of the subject matter described in this specification can be embodied in a medical infusion pump system that includes a portable housing defining a space to receive a supply of insulin; a pump drive system to dispense insulin from the portable housing when the supply of insulin is received in the space; control circuitry that electrically communicates with the pump drive system to control dispensation of the insulin from the portable housing when the supply of insulin is received in the space; a blood glucose detection device comprising at least one of a continuous glucose monitor or a blood glucose meter; a user interface device including a display screen and being configured to receive user input and present one or more outputs on the display screen based on information received from the blood glucose detection device. The user interface device is in communication with the control circuitry and provides a graphic user interface on the display screen that includes a first chart depicting a series of blood glucose values received from the blood glucose detection device aligned over a first axis to reflect the times that the blood glucose values were measured by the blood glucose detection device; and a second chart depicting a series of insulin bolus amounts administered by the pump drive system aligned over a second axis to reflect the times that the insulin bolus amounts were administered; wherein the first axis of the first chart and the second axis of the second chart are time-aligned.

These and other embodiments can each optionally include one or more of the following features. The user interface device can be a mobile computing device in wireless communication with the control circuitry. The mobile computing device can be in direct wireless communication with the blood glucose detection device. The mobile computing device can be in indirect wireless communication with the blood glucose detection device via the control circuitry. The medical infusion pump system can include a second blood glucose detection device; wherein the first blood glucose detection device comprises a continuous glucose monitor; wherein the second blood glucose detection device comprises a blood glucose meter; and wherein the first chart depicts a series of blood glucose values received from the continuous glucose monitor aligned over the first axis to reflect the times that the blood glucose values were measured by the continuous glucose monitor, and a series of blood glucose values received from the blood glucose meter aligned over the first axis to reflect the times that the blood glucose values were measured by the blood glucose meter.

The blood glucose values received from the continuous glucose monitor can be depicted using a first symbol and the blood glucose values received from the blood glucose meter can be depicted using a second symbol, the second symbol being larger than the first symbol. The graphic user interface can further include a current time line that passes through the first axis of the first chart and the second axis of the second chart to identify a current time with respect to the first and second charts; wherein the first chart further depicts a projection of future blood glucose values on a right side of the current time line. The graphic user interface can further includes a third chart depicting a step graph of a plurality of basal insulin delivery rates reflecting rates of basil insulin delivery by the pump drive system aligned over a third axis to reflect times of the basal insulin delivery rates; wherein the third axis of the third chart is time-aligned with the first axis of the first chart and the second axis of the second chart.

The graphic user interface can further include a current time line that passes through the first axis of the first chart, the second axis of the second chart, and the third axis of the third chart to identify a current time with respect to the first, second, and third charts; wherein the first chart further depicts a projection of future blood glucose values on a right side of the current time line; and wherein the third chart further depicts a projected basil insulin delivery rate on the right side of the current time line. The graphic user interface can further include a projected blood glucose value and a time for the projected blood glucose value, wherein the time for the projected blood glucose value is between 15 minutes and 4 hours after a most recent blood glucose measurement. The graphic user interface can further include an arrow indicating a projected profile of how blood glucose values are expected to change over a future time period, the time period being a length of time between 30 minutes and 4 hours.

In general, one innovative aspect of the subject matter described in this specification can be embodied in methods that include the actions of: receiving, at a mobile computing device, a plurality of blood glucose measurement values and corresponding measurement times for each of the blood glucose measurement values from a blood glucose detection device, the blood glucose detection device comprising at least one of a continuous glucose monitor or a blood glucose meter; receiving, at the mobile computing device, information indicating a plurality of insulin bolus dosage values for insulin bolus dosages administered by a pump device of the medical infusion pump system and corresponding bolus administration times for each of the insulin bolus dosage values; displaying, by the mobile computing device, a first graphic user interface having a first selectable input; receiving, by the mobile computing device, user selection of the first selectable input of the first graphic user interface; displaying, by the mobile computing device and in response to receiving the selection of the first selectable input, a second graphic user interface, the second graphic user interface including: a first chart depicting the plurality of blood glucose values received from the blood glucose detection device plotted over a first time axis according to the corresponding measurement times for each of the blood glucose measurement values; and a second chart depicting the plurality of insulin bolus dosage values for insulin bolus dosages administered by the pump device plotted over a second time axis according to the corresponding bolus administration times for each of the insulin bolus dosage values; wherein the first time axis of the first chart and the second time axis of the second chart are time-aligned.

These and other embodiments can each optionally include one or more of the following features. The mobile computing device can be in wireless communication with control circuitry in electrical communication with a pump drive system of the pump device to control dispensation of medicine from the pump device and wherein the bolus dosages administered by the pump device are administered in response to control signals communicated from the mobile computing device to the control circuitry. Receiving the plurality of blood glucose measurement values can include receiving a first plurality of blood glucose measurement values from a continuous glucose monitor and receiving a second plurality of blood glucose measurements from a blood glucose meter. The first chart can depict the first plurality of blood glucose measurement values received from the continuous glucose monitor aligned over the first time axis to reflect the times that each of the first plurality of blood glucose measurement values were measured by the continuous glucose monitor, and the second plurality of blood glucose measurement values received from the blood glucose meter aligned over the first time axis to reflect the times that each of the second plurality of blood glucose measurement values were measured by the blood glucose meter. The blood glucose measurement values received from the continuous glucose monitor can be depicted using a first symbol and the blood glucose measurement values received from the blood glucose meter are depicted using a second symbol, the second symbol being larger than the first symbol.

The second graphic user interface can further includes a current time line that passes through the first time axis of the first chart and the second time axis of the second chart to identify a current time with respect to the first and second charts; wherein the first chart further depicts a projection of future blood glucose values on a right side of the current time line. The second graphic user interface can further include a third chart depicting a step graph of a plurality of basal insulin delivery rates reflecting rates of basil insulin delivery by the pump device aligned over a third time axis to reflect times of the basal insulin delivery rates; wherein the third time axis of the third chart is time-aligned with the first time axis of the first chart and the second time axis of the second chart. The second graphic user interface can further include a current time line that passes through the first time axis of the first chart, the second time axis of the second chart, and the third time axis of the third chart to identify a current time with respect to the first, second, and third charts; wherein the first chart further depicts a projection of future blood glucose values on a right side of the current time line; and wherein the third chart further depicts a projected basil insulin delivery rate on the right side of the current time line.

The second graphic user interface can further include a projected blood glucose value and a time for the projected blood glucose value, wherein the time for the projected blood glucose value is between 15 minutes and 4 hours after a most recent blood glucose measurement. The second graphic user interface can further include an arrow indicating a projected profile of how blood glucose values are expected to change over a future time period, the time period being a length of time between 30 minutes and 4 hours.

The details of one or more implementations of the invention are set forth in the accompanying drawings and the description below. Other features, objects, and advantages of the invention will be apparent from the description and drawings, and from the claims.

DESCRIPTION OF DRAWINGS

FIGS. 4A-4H illustrate various user interface screens of an example bolus calculator for a diabetes management system.

FIGS. 7A-7D illustrate example user interface screens for system maintenance.

FIG. 9A depicts an example alternative user interface dashboard

FIG. 9B depicts an alternative example slide-out navigation screen.

Like reference symbols in the various drawings may indicate like elements.

DETAILED DESCRIPTION

Diabetes management systems provided herein can provide a user experience that reduces the cognitive burden on a person with diabetes (PWD) and their caregivers as they treat the disease. The user experience can be improved by providing a user interface that provides the user with actionable and easy to understand information. In some cases, the user interface can be provided on a mobile computing device (e.g., a smart phone or tablet device), which can be in wireless communication with an insulin pump, a continuous glucose monitor, a blood glucose monitor, and/or other components. Diabetes management systems and methods provided herein may be used and performed, respectively, by a user, for example, a type 1 or 2 diabetes patient or a caregiver of a diabetes patient. In some cases, the systems and methods may be adapted for use with additional chronic diseases or conditions, for example, unresponsive infections, cancer, cancer-related pain, chronic pain, gastrointestinal diseases or disorders, congestive heart failure, hemophilia, immune deficiencies, multiple sclerosis, and rheumatoid arthritis.

Diabetes Management System Overview

Figure 1A:
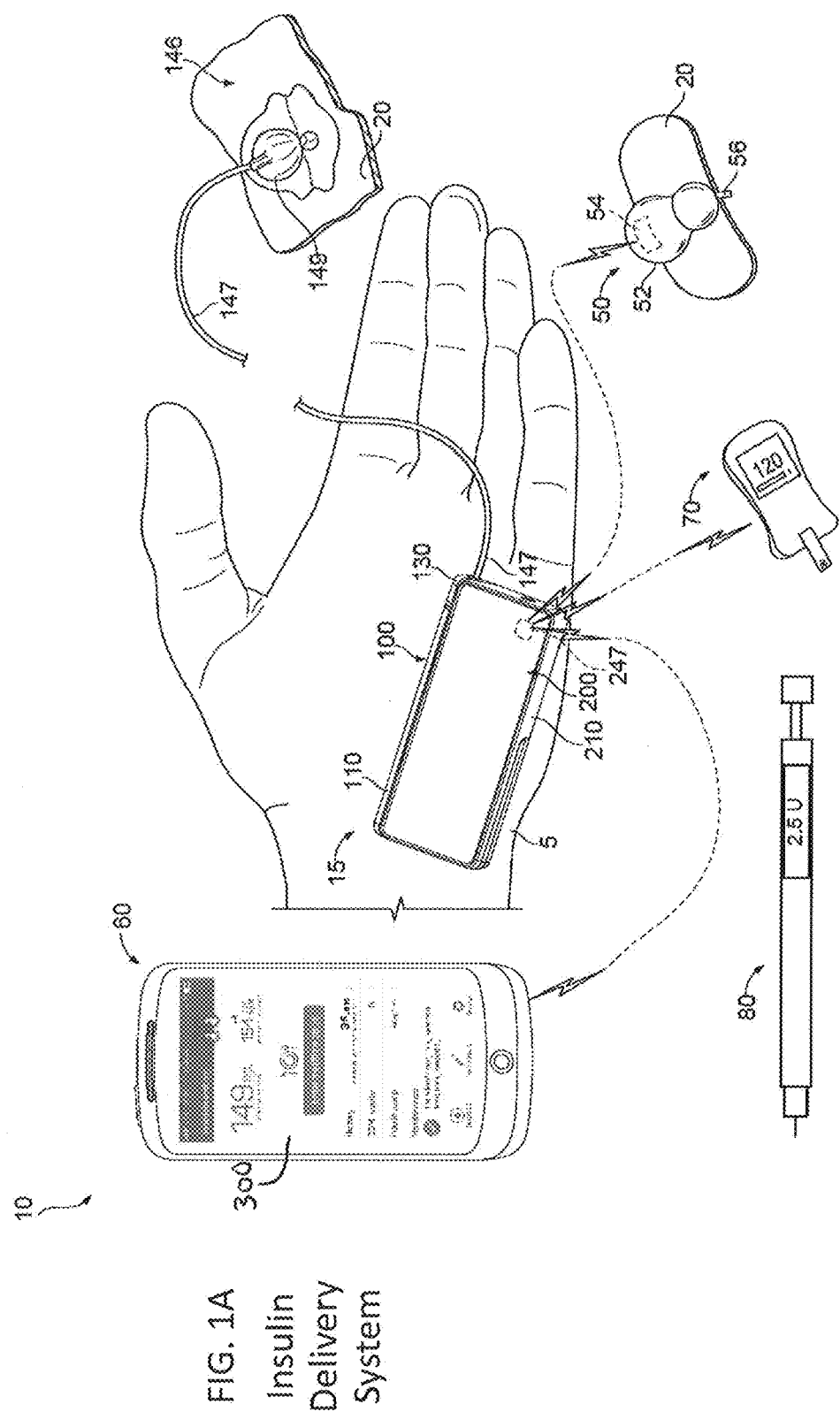
FIG. 1A is an exploded perspective view of an example diabetes management system.
Figure 1B:
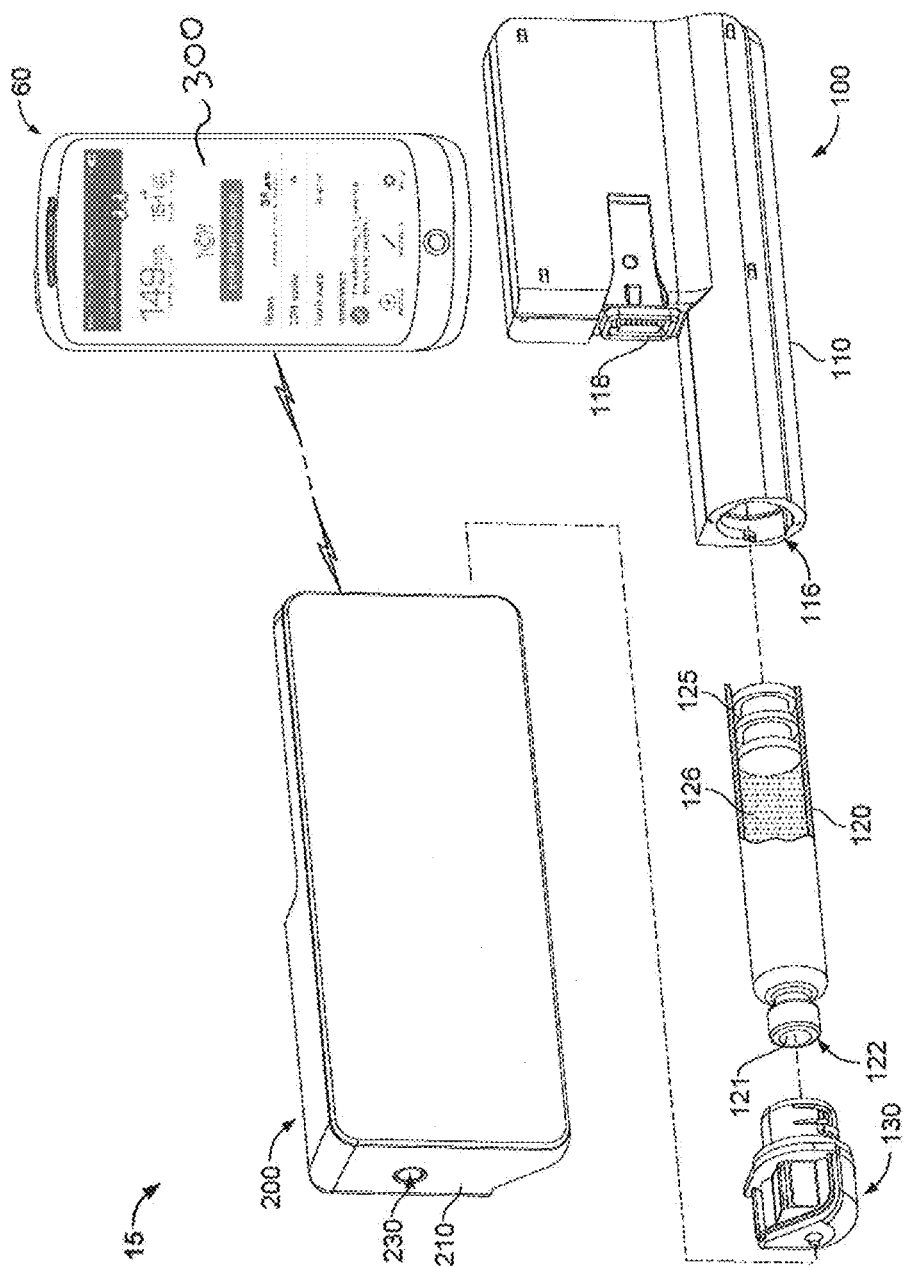
FIG. 1B depicts details of components of an exemplary insulin pump.
Figure 1C:
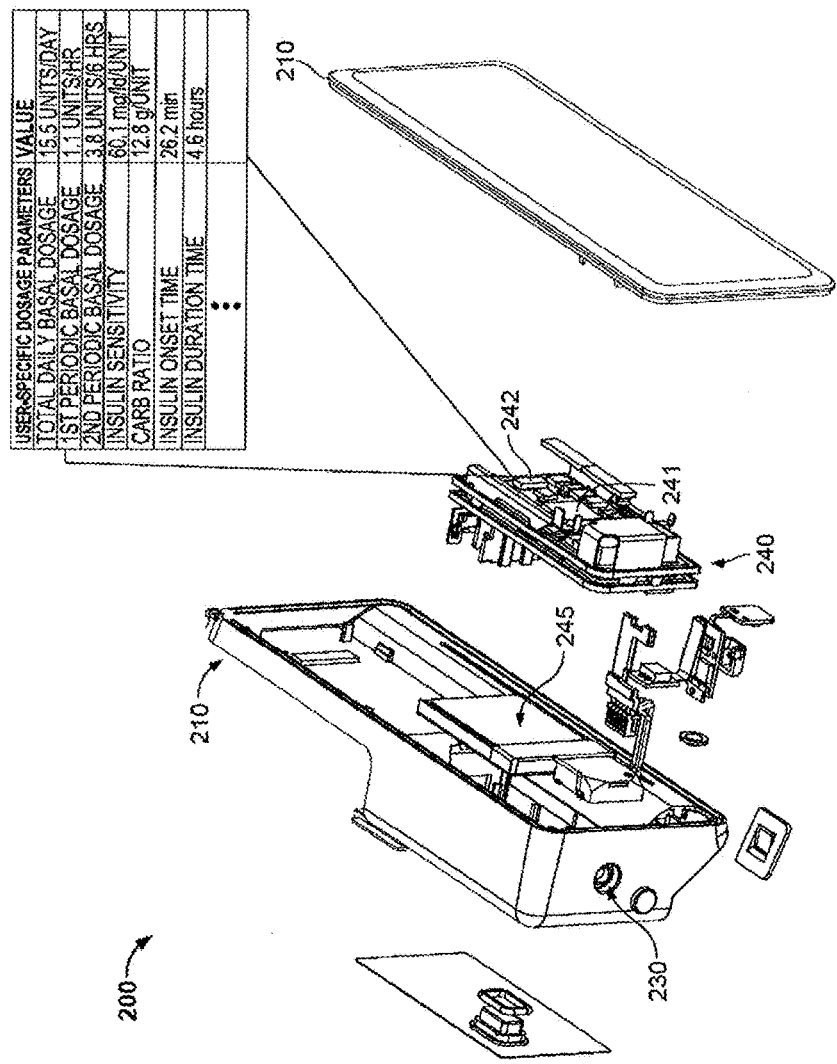
FIG. 1C depicts details of components of an exemplary insulin pump controller.

FIGS. 1A and 1B provide examples of a diabetes management system (DMS) 10 including an insulin pump assembly 15, a mobile computing device 60, a continuous glucose monitor 50, and a blood glucose monitor 70. FIG. 1C depicts the details of an exemplary pump controller, which can be used with DMS 10. Pump assembly 15 includes an infusion set 147 adapted to deliver insulin to an infusion site 146. In some cases, DMS 10 can include an insulin pen 80 or other insulin delivery device that can also be used to deliver insulin to a user. As shown, mobile computing device 60 is in wireless communication with insulin pump assembly 15. As shown, insulin pump assembly 15 is in wireless communication with continuous glucose monitor 50 and data from continuous glucose monitor 50 can be transferred to the mobile computing device 60 via insulin pump assembly 15. In some cases, continuous glucose monitor 50 can wirelessly communicate directly with mobile computing device 60. As shown, insulin pump assembly 15 is in wireless communication with blood glucose monitor 70 and data from blood glucose monitor 70 can be transferred to the mobile computing device 60 via insulin pump assembly 15. In some cases, blood glucose monitor 70 can wirelessly communicate directly with mobile computing device 60. In some cases, blood glucose monitor 70 can be unconnected from the system 10 and a user can manually input a blood glucose monitor reading into mobile computing device 60 (or into insulin pump assembly 15), either with or without a user prompt. In some cases, a blood glucose monitor 70 can be in wireless communication with continuous glucose monitor 50.

The features that are described herein can be extended to DMSs 10 that use alternative insulin delivery devices (e.g., insulin pens, patch pumps, syringes) and/or devices delivering other medicines (e.g., glucagon). In some cases, insulin pen 80 can be in wireless communication with mobile computing device 60. In some cases, user interfaces provided herein can be adapted to allow a user to manually input a bolus delivered using insulin pen 80. User interfaces described herein can also be used with any suitable insulin pump device, including patch pumps and/or other commercially available pumps. In some cases, an insulin pump assembly used in DSM 10 can have a unitary construction and have a reservoir adapted to be filled with insulin.

DMS 10 can be a closed-loop insulin delivery system that uses glucose data from continuous glucose monitor 50 and/or blood glucose monitor 70 in one or more feedback loops to change basal delivery rates, update parameters, settings, and/or models for dosage delivery that are specific to the user. In some cases, a pump controller (e.g., pump controller 200) is part of pump assembly 15 and includes one or more processors adapted to alter basal delivery rates, change parameters, settings and/or models for dosage delivery based on glucose data from a continuous glucose monitor 50 and/or a blood glucose meter 70. In some cases, algorithms for changing basal delivery rates, update parameters, settings, and/or models for dosage delivery that are specific to the user can be present on mobile computing device 60 and/or on a remote server that is accessed by the mobile computing device 60 via the cloud.

Mobile computing device 60 can serve as the user interface of DMS 10. As shown, mobile computing device displays user interface home screen 300, which can allow a user to see actionable data and send commands to pump assembly 15. In some cases, user interfaces provided herein are all present on mobile computing device 60 and are not present on a pump assembly 15, which can eliminate a need for a dedicated display and user input device on pump assembly 15, reducing costs and energy expenditure for pump assembly 15. In some cases, pump assembly 15 can include between zero and five LED indicators adapted to light to inform the user of certain conditions. In some cases, pump assembly 15 lacks a graphical display. In some cases, pump assembly 15 can provide audible, visual, and/or tactile (vibration) alarms to alert a user to a need to access mobile computing device 60 to monitor DMS 10. In some cases, pump assembly 15 lacks any user selectable buttons or icons, but can optionally use an accelerometer to detect motion of the pump assembly 15 for receiving user inputs to the pump assembly 15. In some cases, pump assembly 15 includes between zero and two user actionable buttons or icons. By placing most or all of the user interface on mobile computing device 60 (e.g., a smart phone or tablet device), a user can avoid attracting unwanted attention when inputting data into the DMS. Moreover, smart phones typically have more robust graphical displays, which can improve the user experience as compared to the types of displays typically added to insulin pump devices. In some cases, however, user interfaces provided herein can be present on pump assembly 15, on a web portal, on a continuous glucose monitor controller, on blood glucose meter 70, or another part of a DMS system.

User Interface

Figure 2:
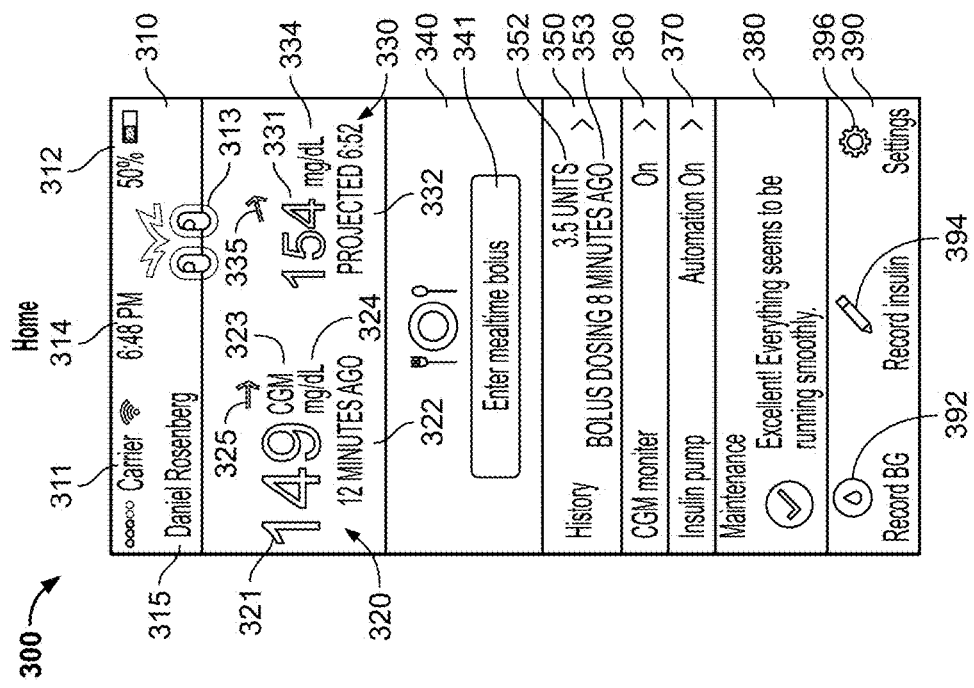
FIG. 2 is an example home screen of a mobile computing application for a diabetes management system.

FIG. 2 depicts an exemplary home screen 300 for DMS 10, which can appear on a mobile computing device 60 when a user selects an icon for the DMS application. If the user is already logged in, home screen 300 can pop up whenever the user selects an icon for the DMS control application. If the user is not logged in, a log-in screen can appear for the user to enter secure identifying information (e.g., a user name and password, a thumb print, an iris scan, etc.). Moreover, as discussed below, the DMS control application can also prompt a user to pair one or more insulin delivery devices, continuous glucose monitors, and/or blood glucose monitors during an initial log in and/or if mobile computing device 60 fails to find a paired insulin delivery device, continuous glucose monitors, and/or blood glucose monitors.

Home screen 300 can provide the user with a simplified view of the DMS status to help the user quickly understand whether the DMS system is operating appropriately and promote routine activities, while also allowing the user to access additional data if the user is interested in more detailed system information. As shown, home screen 300 includes a header 310, which can include mobile and wifi signal strength indicators 311, a mobile computing device power display 312, a logo 313, a time display 314, and a user name 315. Header 310 can provide the user with comfort about the system status of the mobile computing device 60 and assure the user that the mobile computing device 60 is their personal mobile computing device 60.

Home screen 300 includes a most recent glucose measurement field 320 that includes a most recent glucose measurement 321 which can be displayed as the most prominent number, along with a time display 322 of the timing of measurement 320, an identification of the glucose measurement device 323, and the units 324 for measurement 321. In some cases, the most recent glucose measurement 321 can be from a continuous glucose monitor (CGM). In some cases, the most recent glucose measurement 321 can be from a blood glucose meter (BGM). In some cases, the most recent glucose measurement 321 will always display the most recent glucose measurement regardless of the measurement device. Measurement 321 can be the most prominent number because it is typically the number that a person with diabetes (PWD) or a caregiver is most concerned about monitoring to ensure the diabetes is being treated appropriately. Accordingly, a very prominent display of the most recent blood glucose measurement 321 can help assure a user that the DMS is acting appropriately. In some cases, the most recent glucose measurement field 320 can include a trend arrow 325, which can indicate the slope of the recent blood glucose measurements from a continuous glucose monitor.

Home screen 300 can, in some cases, also include a projected condition display 330 indicating how glucose levels are expected to change going forward, which is distinct from the typical display of blood glucose trend indicators, such as trend arrow 325. As shown, home screen 300 displays a numerical projected glucose level 331 along with a future time 332 for which that glucose value is projected and the units 334. In some cases, future time 332 for projected glucose value 331 is between 15 minutes and two hours in advance of the time 321 of the most recent blood glucose value 320. In some cases, future time 332 is between 30 minutes and 1 hour in advance of the time 321 of most recent blood glucose value 320.

Figure 8:
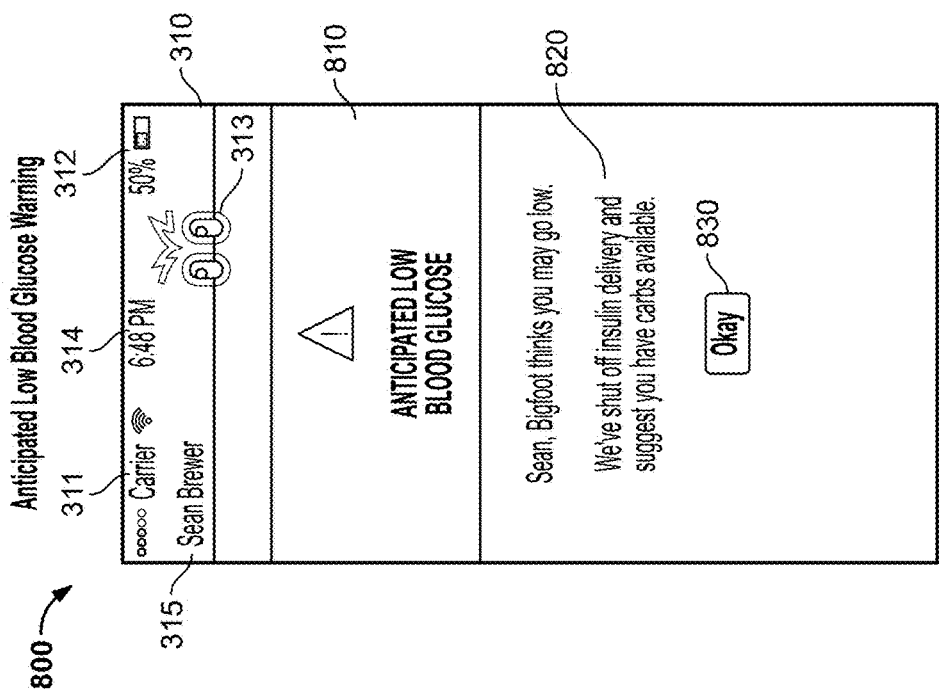
FIG. 8 depicts an example user interface alarm screen.

In some cases, projected condition display 330 can include a prediction arrow 335 that can indicate the direction and/or rate of projected change. As shown, prediction arrow 335 can have a different slope than trend arrow 325, which is because the trend arrow is based on a plot of past glucose data alone. In some cases, prediction arrow 335 is depicted with projected glucose value 331. In some cases, prediction arrow 335 can be present without a projected glucose value 331. In some cases, prediction arrow 335 can be straight to indicate that the glucose values are projected to steadily increase, decrease, or remain relatively static over the next one, two, three, or four hours. In some cases, a slope of prediction arrow 335 can indicate the approximate expected rate of change. In contrast to trend arrow 325, prediction arrow 335 can display the trajectory of projected glucose values, not just the trajectory of previously recorded glucose values. In some cases, prediction arrow 335 can be curved to indicate that projected glucose levels are expected to rise then fall (e.g., after a meal and bolus) or fall then rise (e.g., after the system has detected a projected low and reduced basal delivery rates). In some cases, projected condition display 330 can include a text string with or without prediction arrow 335 and/or projected glucose value 331 to indicate how the DMS 10 expects glucose values to change over the next 15 minutes to 4 hours. Exemplary text strings could include the following: "Glucose values expected to remain with 20 mg/dL of target over the next two hours"; "Glucose values expected to rise over the next hour, but return within 20 mg/dL of target within three hours"; "Glucose values expected to fall over the next 30 minutes to be within 20 mg/dL of target"; "Glucose values projected to continue to rise, DMS recommends a correction bolus"; and "Glucose values projected to fall quickly, DMS recommends that you eat sugar or inject glucagon." In the case that the DMS projects a high or low that cannot be corrected with an adjustment to a basal rate using a closed loop algorithm, the DMS system can provide an alarm (for example, on the mobile computing device 60, pump assembly 15, or a combination thereof) to get the user's attention, thus the typical display of projected glucose values should reassure the user that the DMS 10 is acting appropriately to manage the PWD's diabetes. For example, the DMS 10 can perform an analysis to determine if a projected high or low BGL can be corrected with an adjustment to a basal rate. If the DMS 10 determines that the BGL cannot be corrected with an adjustment to the basal rate, the DMS 10 provides an audio, visual, and/or tactile alarm to alert the user to the projected high or low. An example alarm is depicted in FIG. 8, discussed below. An advantage of a projected glucose value 331, a prediction arrow 335 depicting how glucose values are expected to change, and/or a text string explaining how glucose values are expected to change over the next few hours is that the user does not need to conduct a self-evaluation that considers trends in the glucose data, amounts of food consumed, and amounts of recently insulin delivered to evaluate whether the DMS is operating appropriately.

In some commercial devices, an amount of insulin on board (IOB) is calculated to tell a user an estimate of how much insulin has been delivered but not yet acted, which some diabetics use to adjust treatment. In some cases, home screen 300 can display an indication of an amount of insulin on board (IOB) in order to reassure users that are accustom to seeing an IOB. In some cases, home screen 300 can eliminate an IOB display due to the presence of a projected glucose value, a projected glucose trajectory, or a textual string. In some cases, a user can set an option regarding whether to see an IOB value on home screen 300. For example, a setup screen can provide a control that allows the user to elect to display an IOB value on the home screen or on another screen.

Referring back to FIG. 2, home screen 300 includes a history field 350 configured to indicate to the user the most recent relevant event, which can typically be a bolus amount 352 along with the timing 353 of the bolus. History field 350 can ensure that a user can quickly confirm that a recent bolus (e.g., for a recent meal) was delivered. Bolus history display 350 is a more intuitive way for a user, especially users new to the management of diabetes, to understand the currently enacted treatment. If a user clicks on history display 350, a history user interface can appear, such as those discussed below in relationship to FIGS. 3A and 3B.

History User Interfaces

Figure 3B:
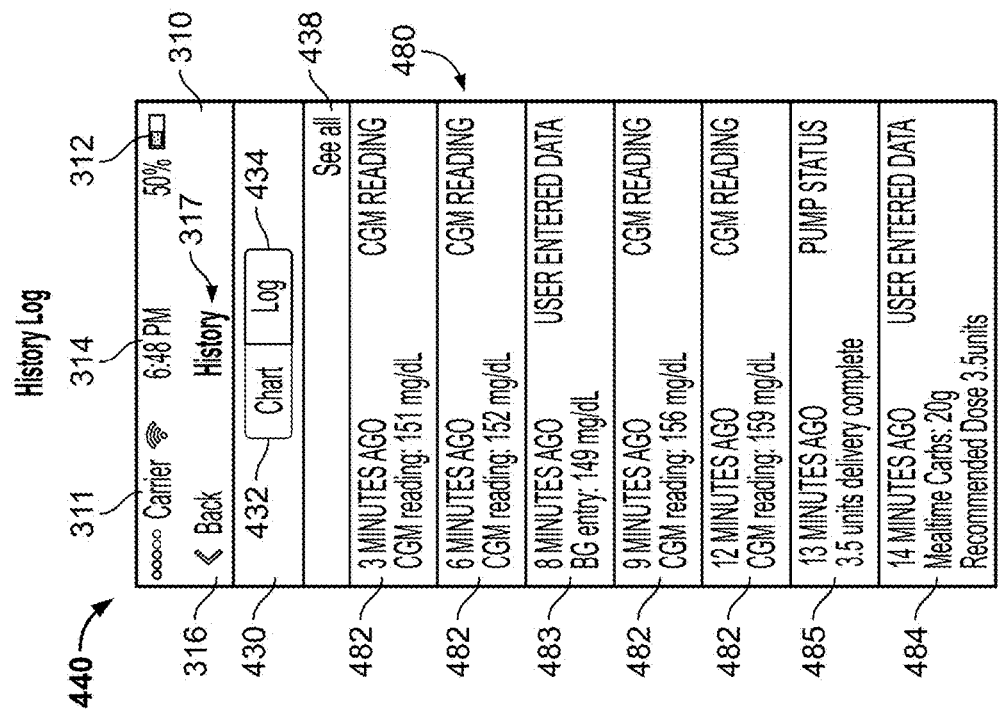
FIG. 3B is an example history log for a diabetes management system.
Figure 3A:
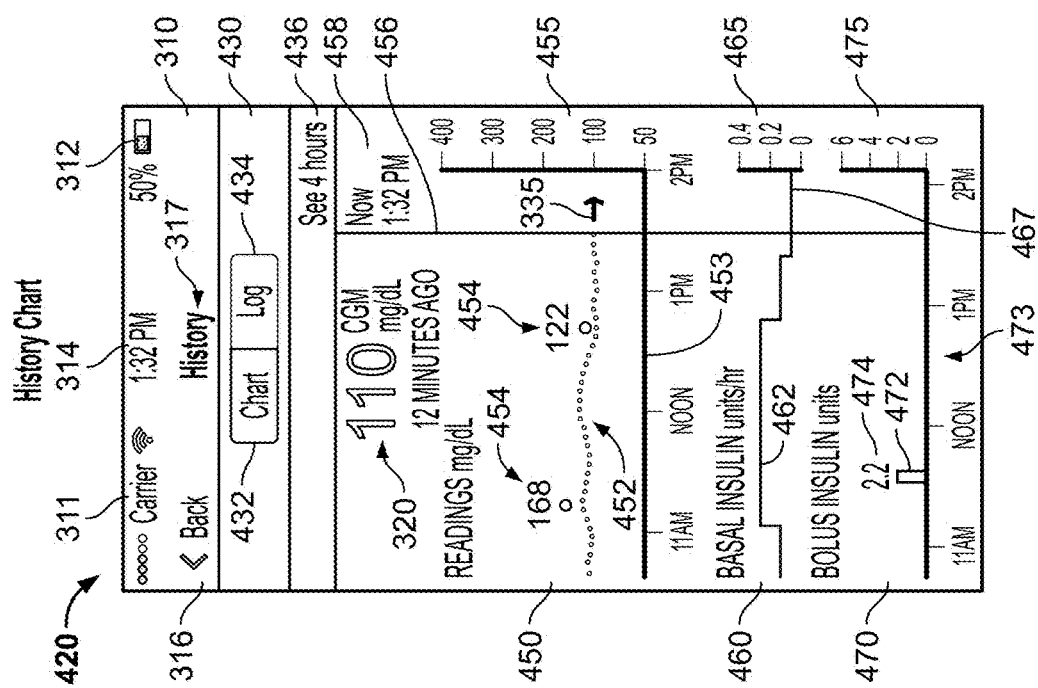
FIG. 3A is an example history chart for a diabetes management system.

When a user clicks on the history field 350 on home screen 300, the user can arrive at one of the history screens 420 or 440 depicted in FIGS. 3A and 3B. As shown, screens 420 and 440 both include headers 310 similar to the header on home screen 300, but having a title 317 and a back button 316. Back button 316 can bring the user back to home screen 300. A toggle field 430, below header 310, allows a user to toggle between history screens 420 and 440 by clicking on chart control 432 for history chart screen 420 and by clicking on log control 434 for history log screen 440.

History chart screen 420 provides time-aligned graphical charts 450, 460, and 470. Glucose value chart 450 shows both continuous glucose monitor glucose values 452 and blood glucose meter glucose values 454 plotted along a time x-axis 453 and a glucose value y-axis 455. As shown, blood glucose meter and continuous glucose meter values are visually distinct (e.g., different color, different size, etc.). In some cases, data 454 from a blood glucose meter is more prominent because blood glucose meter data is more accurate and less frequent. In some cases, data 454 from a blood glucose meter can display the numerical value of the reading to make it clear that the data point is more accurate. A current time indicator line 456 extends down the screen and a time indicator 458 indicates the current time. The data to the left of time indicator line 456 is historical data, while the data to the right of the indicator line 456 can be blank, can project one or more predicted glucose values (for example, in a different color or using a different dash pattern), or can project a range of possible glucose values. As shown, the data to the right of indicator line 456 can include prediction arrow 335 having a shape and/or slope as discussed above. In some cases, projected glucose values can appear like a shaded triangle to indicate a range of possibilities. Beneath glucose value chart 450, charts 460 and 470 depict the basal delivery rates 462 over time and a history of bolus deliveries over time, respectively. Basal dosage chart 460 indicates the basal delivery rates, which DMS 10 automatically adjusts based on data from a continuous glucose monitor, blood glucose meter, and/or recent insulin deliveries. The y-axis 465 of basal dosage chart 460 includes basal delivery rates per hour. On the right side of time indicator 456 basal dosage chart can be blank or display the currently scheduled basal delivery rate 467. Although actual basal insulin may be delivered as discrete units at regular or irregular intervals based on the specifics of the insulin pump, chart 460 depicts the basal delivery as a step graph 462 showing a continuous insulin delivery as a rate over time. Bolus dosage chart 470 depicts a history of larger dosages of insulin 472 along the time x-axis 473 as bars 472 on a graph with units of insulin along the y-axis 475. Each bar can include a numerical display 474 of units delivered. In some cases, charts 460 and 470 are separate due to the different y-axis units. In some cases, charts 460 and 470 can overlie each other and each bolus bar labeled to indicate the amount of the bolus, such as depicted in the alternative user interface depicted in FIG. 9A. The history screen 420 can typically display 4 hours of data, but a user can click on 436 to change the amount of time displayed.

History Log screen 440 can provide a log 480 of all glucose readings 482 and 483 (both from a continuous glucose monitor and a blood glucose meter, respectively) and insulin delivery tasks 484 and 485 (e.g., bolus deliveries and/or changes to basal insulin rates) as separate entries, each with a time, a label, and a summary. A filter 438 can be used to select the types of data displayed in log 480.

After a user has gained confidence in the DMS, a user might not typically access history screens 420 and 440. Nonetheless, the presence of history screens 420 and 440 can allow a user to gain trust in the DMS by allowing the user to see all activates. Moreover, users might access history screens 420 and 440 if the user believes that the system is acting unusually. Additionally, clinicians and other care providers can use history screens to monitor the DMS to determine if the DMS is acting appropriately.

Bolus Entry

Referring back to FIG. 2, in some cases home screen 300 also prominently displays a bolus entry user actionable display 340, including an icon 341, that allows a user to enter carbohydrates and/or units of insulin to properly dose insulin in response to a meal. The button for bolus entry user actionable display 340 is prominently displayed because it is expected to be the most common action of a user using a closed-loop diabetes management system. For example, the button for bolus entry can be displayed as larger than any other single control on the home screen 300. Home screen 300 can additionally include additional user selectable icons that allow the user to provide additional data to DMS 10, but less routine tasks (e.g., recording outside insulin) can be deemphasized as compared to more routine tasks (e.g., inputting a mealtime bolus). As shown in FIG. 2, navigation row 390 can include additional user selectable icons.

Figures 4A, 4B:
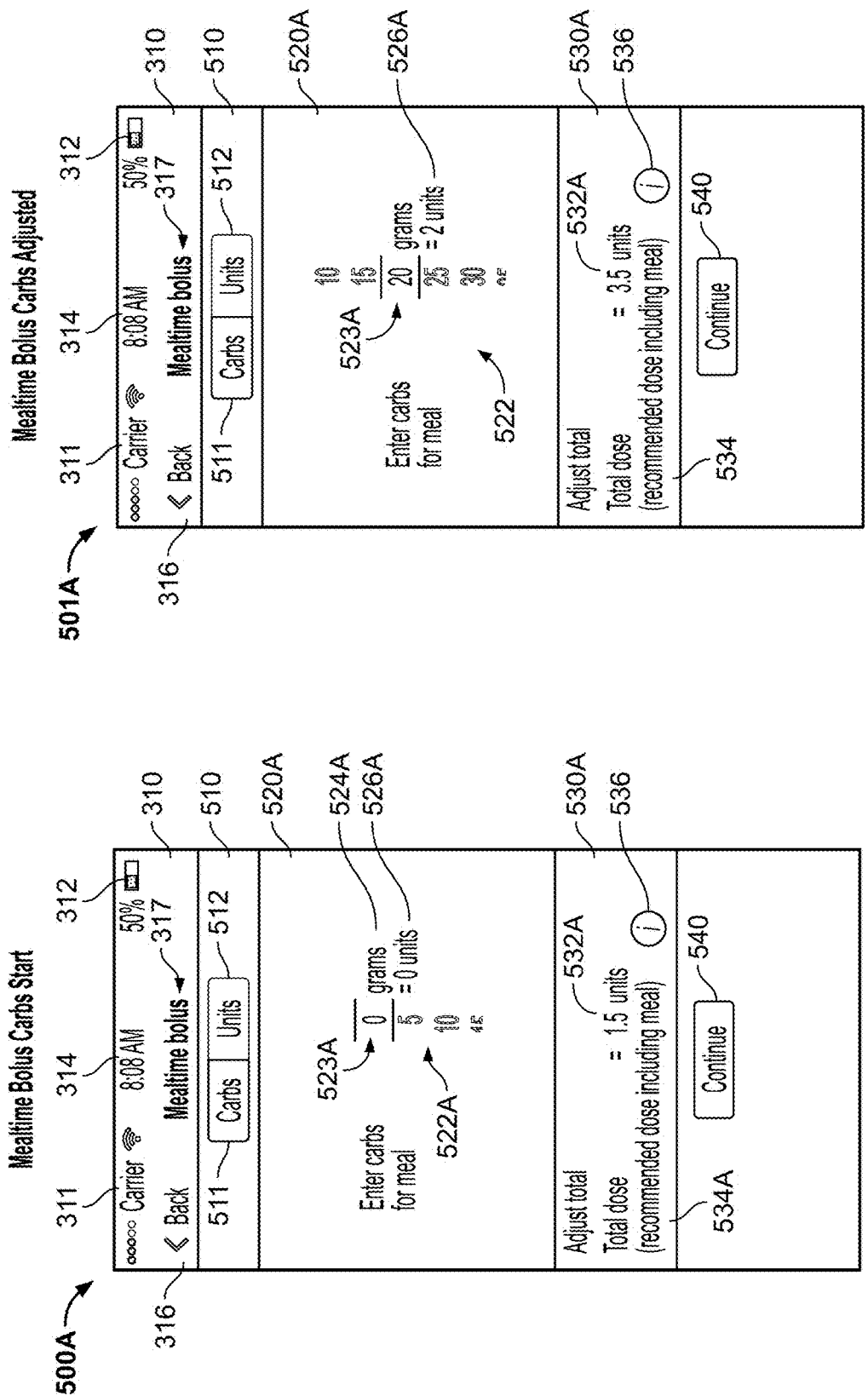

When a user selects the bolus entry field 340 or icon 341, a user can be delivered to a bolus calculator screen, such as screen 500A as depicted in FIG. 4A. The bolus calculator thus minimizes the amount of information that the user must comprehend when considering a mealtime bolus. FIGS. 4A-4G depict how a bolus calculator can be used. Again, the bolus calculator screens include a heading 310 that can include a title 317 and a back button 316, which can be clicked to return to home screen 300. Beneath header 310, a toggle field 510 allows a user to switch between entering carbs consumed and units of insulin by selecting carbs control 511 or units control 512. As shown in FIG. 4A, the carbs control 511 is selected. If the units control is selected, the user will be delivered to screen 500C as depicted in FIG. 4G. The toggle between carbs and units of insulin allows for different users to use the bolus calculator, as some users may think about meals in terms of the number of carbohydrates consumed while others think about meals in terms of units of insulin needed for the meal.

In screen 500A, a user first scrolls down to a number of carbs 523A using scroll wheel 522A to estimate a number of carbs for the meal, changing the screen to appear similar to screen 501A depicted in FIG. 4B. The units 524A for the scroll wheel 522A are clearly displayed to avoid user confusion about the data being entered. As the grams of carbs 523A is adjusted using scroll wheel 522A, the user interface dynamically updates a conversion of the carbs 523A to units of insulin 526A for the user, which can be based on the user's carbohydrate to insulin ratio. Screens 500A and 501A further depict a total dose field 530A that includes an adjusted total amount of insulin delivery 532A that displays a calculated correction of the dose. Text string 534A can indicate that the DMS recommends the calculated correction of the dose. An information button 536 can be clicked on to explain to a user how this is calculated. An example of the information that can be included on the screen when clicking 536 is shown in screen 537 in FIG. 4F, discussed below. When the user first arrives at the bolus calculator screen and the carbs scroll wheel 522A initially has the selected carbs value 523A set to zero, the total dose 532A will indicate the amount of the adjustment, so a user can see how much of an adjustment the DMS is making. This adjustment can be based on factors such as the amount of insulin on board, current glucose values and/or trends, and/or additional information about the user.

Figures 4C, 4D:
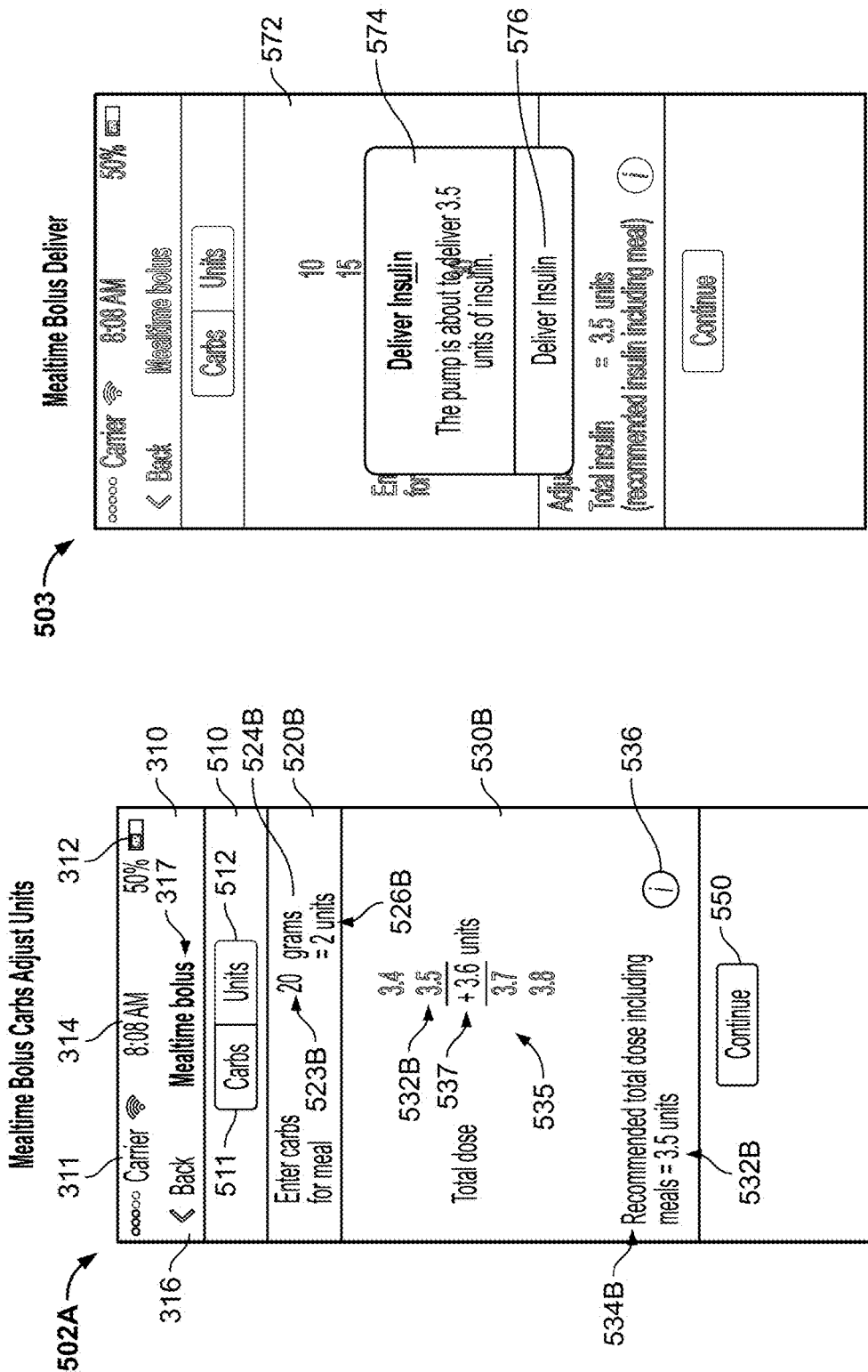

Once the user has entered the number of carbs (which can be left at zero), the user can select continue button 540 to go to screen 502A as depicted in FIG. 4C. In some cases, the text of continue button 540 can instead recite "Adjust Insulin." After selecting continue button 540, the fields 520A and 530A change to fields 520B and 530B as shown in FIG. 4C. In field 520B, the user selected number of carbs 523A is displayed as the selected number of carbs 523B without any scroll wheel to indicate that this value is set. Field 520B also displays the units 524B and the conversion to units of insulin 526B so that the user can remember the amount of units being delivered due to the consumption of food. If the user wishes to change the number of carbs entered, the user can click on field 520B to have the screen revert to screen 501A. Field 530B then allows the user to make a personal adjustment using a scrolling wheel 535 to the total dose. The recommended total dose 532A from screen 501A can appear at the bottom of field 530B and/or have a distinct appearance in the scrolling wheel 535 to remind a user what the DMS has calculated for the total dose. Screen 502A allows the user to adjust the number of units so that the user has ultimate control over the bolus amount. For example, a user may want the adjust the bolus amount from the DMS calculated amount if the user is feeling sick or if the user is about to exercise. Being able to adjust the number of units for the total dose 537 can be useful when a user is building trust in the system. Once the user has selected the total dose 537 on scroll wheel 535, the user can hit continue button 550 to bring up screen 503. In screen 503, depicted in FIG. 4D, a confirmation box 574 pops up to inform the user that the pump is about to deliver a certain number of units of insulin to the user and has the user click on selectable button 576 to deliver the insulin. The display of box 574 results in the reminder of the screen being shaded 572. FIG. 4E depicts a screen 504 indicating an announcement 360 that insulin has been delivered successfully. In some cases, a screen can appear showing the progress of the bolus. For example, a user interface can show a progress bar.

FIG. 4F displays a bolus information box that can be displayed when a user selections information icon 336 in any of FIGS. 4A-4C, 4G and 4F. Screen 537 explains how the recommended dose is based on an insulin to carb ratio and blood glucose readings 538A and explain that a user can manually adjust the total 538B. The box can be over a shaded background 572. A user can select an "OK" button 539 to exit the information box.

FIGS. 4G and 4H illustrate how the bolus calculator works if the user clicks on units control 512 to arrive at screen 500C and enters units 523C using a scroll wheel 522C. A conversion of the units 523C into a number of carbs 526C dynamically updates. Again, the units 524C is clearly displayed so that a user knows what is being entered. A total dose recommendation field 530C is also dynamically updated to display a calculated total dose 532C. Once a user hits continue button 540, the user is brought to a screen similar to screen 502A, as depicted in FIG. 4C, to allow the user to manually adjust and deliver an amount of insulin using similar functionality. In some cases, an alarm is scheduled for a predetermined number of minutes (e.g., 5 minutes) in the future as soon as the bolus screen is activated, and cleared upon the delivery of the insulin so that a user that inadvertently fails to deliver the bolus can be reminded that they may have intended to deliver a bolus. For example, this could be useful if the application is interrupted and the user is unsure if the bolus instruction was delivered to the insulin pump and/or forgets to finish to bolus delivery process. In some cases, the alarm can be set on pump controller.

DMS Operating Information

Referring back to FIG. 2, home screen 300 can include a CGM monitor field 360 and an insulin pump field 370 to display relevant information about whether these devices are properly connected and/or the mode of operation. For example, in order for a closed loop system to be in operation, the system requires proper access to the continuous glucose monitor (CGM) data, thus, indicating that the CGM Monitor is "ON" will assure the user that the DMS 10 is operating appropriately. If the user clicks on the CGM monitor field 360, the user can go to a screen where the user can adjust the continuous glucose monitor settings. In some cases, predicting field 330 is only displayed in response to the CGM monitor being on. In some cases, when the CGM monitor is off, the system will display a warning in predicting field 330 that the system cannot predict future glucose values because the CGM monitor is not operating.

In some cases, a user can select CGM monitor field 360 to make changes to the settings or to tell the DMS to stop using data from a paired continuous glucose monitor. For example, if a user suspects that the data from a paired continuous glucose monitor is inaccurate, a user can turn the CGM indicator to "OFF" so that the DMS will stop using glucose values from the continuous glucose monitor, which will stop any adjustments to basal insulin delivery rates from predetermined basal delivery rates. In some cases, the CGM monitor field 360 will be turned "OFF" during a warmup period after a new continuous glucose monitor sensor has been placed on the user.

Displaying the status of the insulin pump in field 370 is also useful to assure the user that the system is operating appropriately. In some cases, DMS can have a plurality of operating modes depending on the data available. For example, some modes may automate basal delivery rates based on CGM data in order to provide a closed loop system. Accordingly, displaying that automation is on for the insulin pump can assure the user that the DMS will automatically adjust basal delivery rates in order to control blood glucose levels.

Additional Data Entry Field

Referring again to FIG. 2, home screen 300 can also include navigation row 390 along the bottom of the device, which can display other user-selectable icons for less routine tasks. As discussed above, these tasks may be less frequent than mealtime boluses because they represent information that can be collected via wireless connections between a blood glucose meter 70, the pump assembly 15, and the continuous glucose monitor 50. As shown in FIG. 2, in some cases navigation row 390 can include a recording BG icon 392, recording outside insulin icon 394, and settings icon 396. Additional possible icons could include icons, for example, that allow a user to indicate exercise, sickness, sleep, and/or additional states that could impact blood glucose levels.

Figure 5:
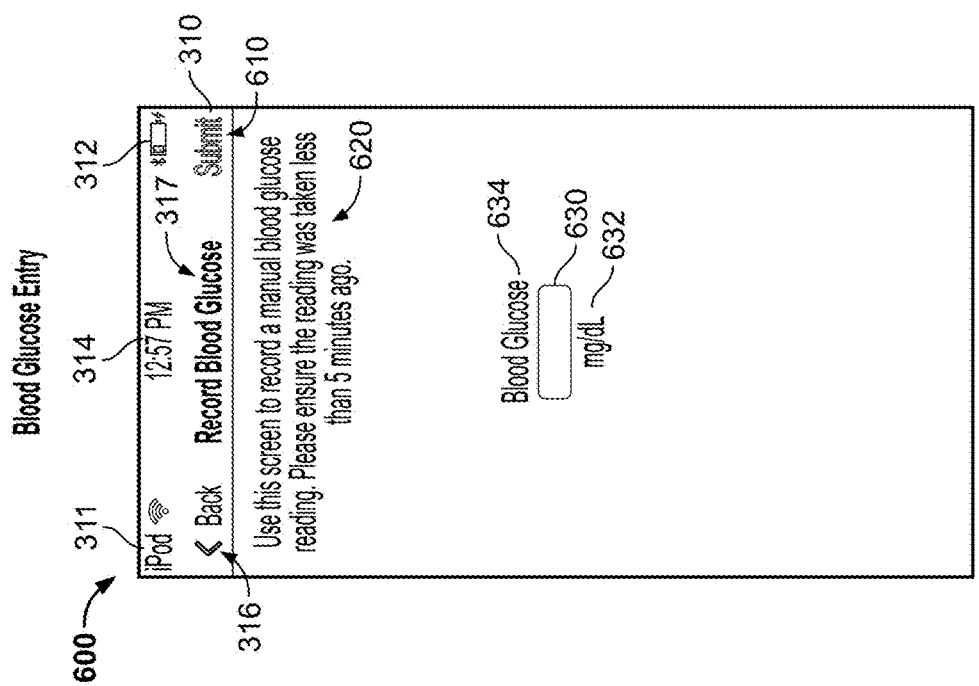
FIG. 5 illustrates an example user interface for entering a blood glucose value.

When a user selects icon 392 to input a blood glucose meter reading, a screen similar to screen 600, as depicted in FIG. 5, can appear. Screen 600 can include a header 310 similar to those discussed above, but also include a submit button 610. Screen 600 can include a warning about when the reading must have been taken 620, and an input field 630 for the blood glucose meter value. Screen 600 clearly includes a label 634 identifying the field as being for blood glucose and provides the units 632. In some cases, blood glucose measurement can be used to calibrate the continuous glucose monitor of the DMS. When a user clicks on field 630, a numerical keypad can appear to allow the user to enter a number and hit return. In some cases, screen 600 can pop up as part of completing the bolus calculator. As discussed above, DMS systems provided herein can include blood glucose meters in wireless communication with an insulin pump and/or a mobile computing device, thus the manual entry of blood glucose values may not be a typical action of a user.

Figure 6:
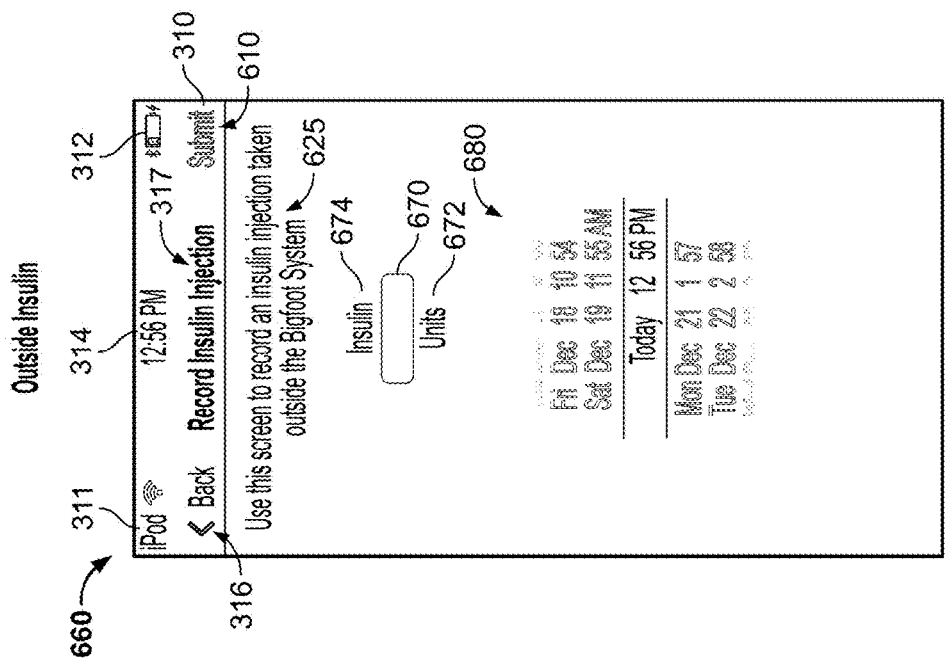
FIG. 6 illustrates an example user interface for reporting outside insulin.
Figures 7A, 7B:
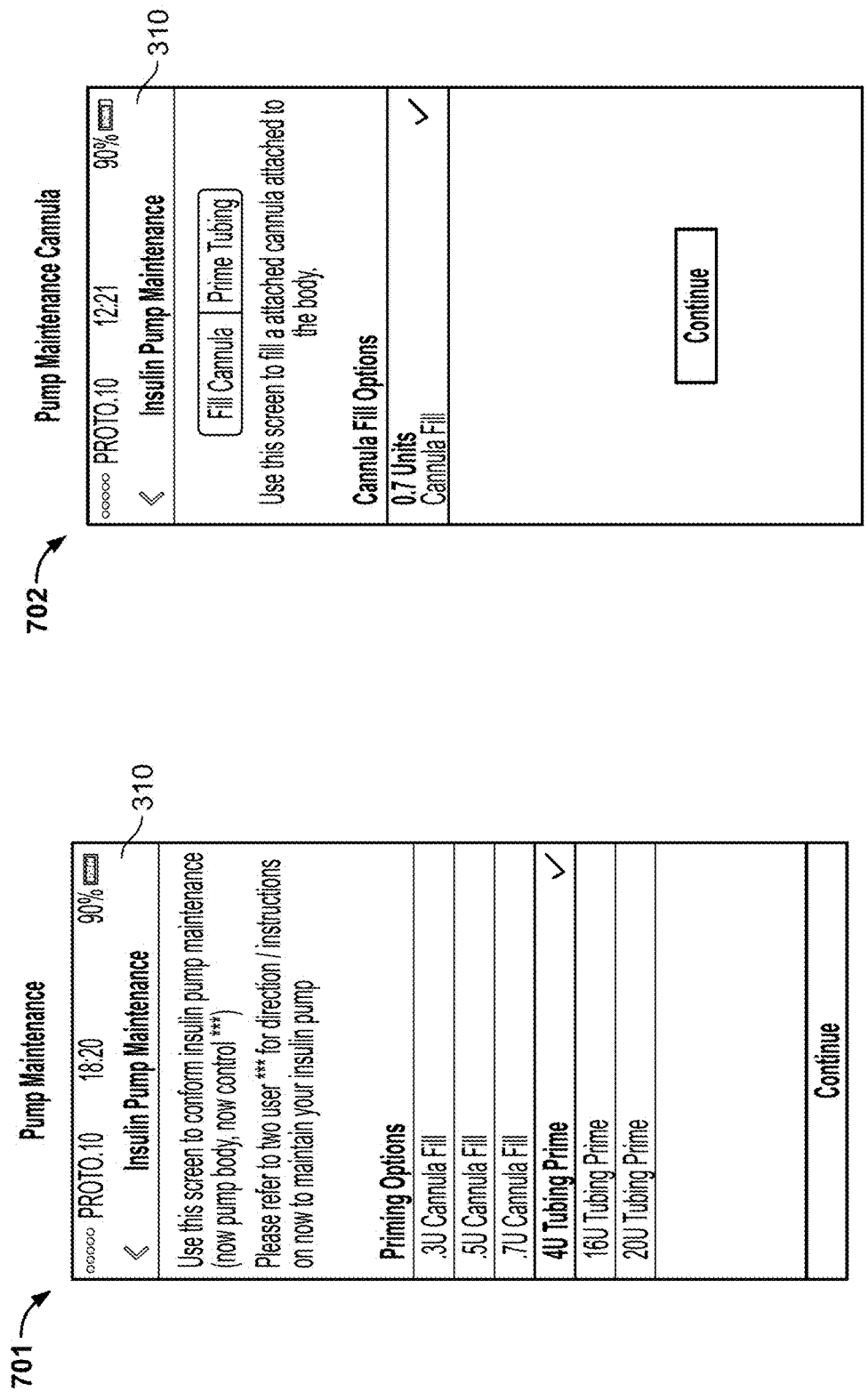

When a user selects icon 394 to enter outside insulin, a screen similar to screen 660, as depicted in FIG. 6, can appear. Screen 660 can include a header 310 similar to those discussed above with a submit button 610, a warning about the insulin being insulin taken outside of the DMS system 625, and an input field 670 for entering a number of units 672 of outside insulin. Field 670 is clearly labeled as being insulin 674. Screen 660 also includes a time scrolling wheel 680 for a user to enter the time that the insulin was administered. In some cases, screens similar to screen 660 can allow for entry of different types of medication (e.g., glucagon), different types of insulin (e.g., slow acting insulin), and/or other information about how the medication was delivered.

When a user selects icon 396 (FIG. 2) to adjust settings, the user can adjust a number of other user settings, such as insulin sensitivity factors, carbohydrate to insulin ratios, baseline basal insulin delivery rates, and target glucose levels.

Maintenance Field

Home screen 300 also includes a maintenance field 380 adapted to indicate to a user if the user will be expected to conduct any maintenance tasks in the near future (e.g., in the next 24 hours) and/or whether the DMS has detected any need for immediate maintenance. For example, maintenance field 380 can indicate when an infusion set is due for replacement, when an infusion set should be changed, when disposable parts of a pumping assembly need to be replaced and/or when an insulin reservoir needs to be refilled, when the continuous glucose monitor sensor needs to be changed or moved to a new location on the body, or when a blood glucose measurement should be made to calibrate the continuous glucose monitor. In some cases, static indicators can indicate the approximate deadline for conducting routine maintenance, optionally with color indicators indicating the urgency of each maintenance task (e.g., red, yellow and green to indicate high, medium, and low urgency respectively). In some cases, maintenance field 380 can indicate that no maintenance tasks are required. In the cases that immediate maintenance is required, DMS 10 can provide an alarm (e.g., on the mobile computing device 60, pump assembly 15, or a combination thereof) to get the user to look at the user interface to learn about the required maintenance task. Maintenance field 380 is configured to reassure a user that system maintenance tasks are up-to-date, thus again reducing the cognitive burden on the user.

FIGS. 7A-7D depict pump maintenance user interfaces 701-704, which can be used when conducting pump maintenance. User interface 701 allows a user to select between conducting cannula fill operations and tube priming operations. User interface 702 confirms a cannula fill. User interface 703 provides options for a tubing prime operation. User interface 704 provides a warning that the tubing is about to be primed including a confirmation text box 774 over a shaded background 772.

Alarm Screen

FIG. 8 depicts an alarm screen 800 that includes a header 310 similar to those discussed above, and an alert field 810 and a text field 820. Alert field can be colored to indicate that an immediate action is needed. For example, field 810 can have a red background. Text field 820 can inform the user, potentially by name, that the DMS is taking a limited action but that the user may want to take additional action. An "OK" or "Okay" bottom can be present at the bottom of screen 800 for the user to acknowledge the alarm.

Alternative Home Screen and Navigation

FIGS. 9A and 9B depict an alternative dashboard having slide-out navigation to access various tasks. Dashboard 900 includes a graphical history display similar to that shown in FIG. 3A, discussed above, but uses this graphical display as part of a home screen. Dashboard 900 includes a header 910, similar to header 310 discussed above, that includes mobile computing device connection information, a mobile computing device power indicator, and a time of day. Beneath header 910, dashboard displays an estimate of the insulin on board (IOB) 930 and a most recent glucose measurement 932, and an arrow 933 showing a prediction of how blood glucose levels will change, similar to prediction arrow 335 discussed above. In some cases, dashboard 900 can include an alert icon 920 that appears if there is an alarm condition, which the user can select to learn details about the alert.

Dashboard 900 further indicates when the most recent blood glucose measurement was taken. Chart 940 is similar to chart 450 discussed above, but can use different colors. Chart 950 is similar to charts 460 and 470 discussed above, but can include an overlay of the bars representing bolus deliveries and the step graph showing the basal rate. User-selectable icons along a bottom row 960 can allow a user to input a blood glucose measurement, icon 962, enter a meal for a bolus calculation, icon 962, and look at user settings, icon 964. Clicking on icon 962 can bring the user to the user interface of FIG. 5. Clicking on icon 964 can bring the user to the bolus calculator discussed above in relationship to FIGS. 4A-4G.

By clicking on navigation icon 970 in the upper left corner, a slide-out menu can appear, as shown as screen 901 in FIG. 9B. The navigation slide-out can include icons for recording outside insulin, changing device pairings, editing configurations, preforming insulin pump maintenance, preforming insulin infusion set maintenance, starting insulin delivery, starting a continuous glucose monitor sensor, changing the automation mode, and viewing the event history.

Exemplary Mobile Computing Device

Referring again to FIGS. 1, 1B, and 1C, mobile computing device 60 can communicate with the controller device 200 through a wireless and/or wired connection with the controller device 200 (e.g., via a Bluetooth wireless communication connection in this particular implementations). In some cases, mobile computing device 60 communicates wirelessly with other elements of the system 10. Mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases where there is no computing device 200 that is part of a pump, the mobile computing device 60 can receive and log data from the other elements of system 10. In some cases, a user can input relevant data into mobile computing device 60. In some cases where a pump assembly 15 includes controller device 200, the mobile computing device 60 can receive and log data that is collected by the controller device 200, such as blood glucose readings, dosage delivery information, and also can receive user inputs (e.g., user-selected parameters to be stored on the controller device 200, user-confirmation of bolus dosages (described below), and others). In some cases, mobile computing device 60 can be used to transfer data from controller device 200 to the cloud. In some cases, the mobile computing device 60 provides a user interface (e.g., graphical user interface (GUI), speech-based user interface, motion-controlled user interface) through which users can provide information to control operation of the controller device 200 and the insulin delivery system 10. For example, the mobile computing device 60 can be a mobile computing device running a mobile app that communicates with the controller device 200 over short-range wireless connections (e.g., BLUETOOTH connection, Wi-Fi Direct connection) to provide status information for the insulin delivery system 10 and to allow a user to control operation of the insulin delivery system 10 (e.g., toggle between delivery modes, adjust settings, log food intake, confirm/modify/cancel bolus dosages, and the like).

Continuous Glucose Monitor

Continuous glucose monitor 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In some cases, the sensor shaft 56 can measure glucose or another analyte in interstitial fluid or in another fluid and correlate that to blood glucose levels. In response to the measurements made by the sensor shaft 56, continuous glucose monitor 50 can employ the wireless communication device 54 to transmit data to a corresponding wireless communication device 247 housed in the pump system 15. In some cases, the monitoring device 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the monitoring device 50 can employ other methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative implementations, the monitoring device 50 can be in communication with the controller device 200 or another computing device via a wired connection.

Blood Glucose Meter

DMS 10 may optionally communicate with blood glucose meter 70 in addition to (or as an alternative to) continuous glucose meter 50. For example, one or more test strips (e.g., blood test strips) can be inserted into a strip reader portion of blood glucose meter 70 and then receive blood to be tested. In some cases, blood glucose meter 70 is configured to analyze the characteristics of the user's blood and to communicate (e.g., via a Bluetooth wireless communication connection) the information to the controller device 200. In some cases, a user can manually input a glucose meter reading. Blood glucose meter 70 can be manually operated by a user and may include an output subsystem (e.g., display, speaker) that can provide the user with blood glucose readings that can be subsequently entered into the controller or user interface (to collect the data from an unconnected BGM into the system). Blood glucose meter 70 may be configured to communicate data (e.g., blood glucose readings) obtained to the controller device 200 and/or other devices, such as the mobile computing device 60. Such communication can be over a wired and/or wireless connection, and the data can be used by the controller device 200 and/or the mobile computing device 60 to perform multiple delivery modes and/or a secondary feedback loop for the insulin delivery system 10.

External Insulin Delivery Devices

DMS 10 may include one or more external medication delivery devices 80 (e.g., syringe, an insulin pen, a smart syringe with device communication capabilities, or the like) through which additional medicine dosages (e.g., insulin, glucagon) can be manually administered to a user. In some cases, user interfaces provided herein allow users to input a medication, a dosage amount, and the timing so that a closed-loop control algorithm can account for the additional medication. In some cases, mobile computing device 60 can make a recommendation for an amount of insulin to be delivered using an external delivery device.

Pump Assembly

Referring again to FIG. 1, pump assembly 15 can include pump device 100 configured to removably attach to the controller device 200 in a manner that provides a secure fitting, an overall compact size, and a reliable electrical connection. Additional details about the particularly depicted pump assembly 15 are described in more detail below in connection with FIGS. 1B and 1C.

Pump assembly 15 can be pocket-sized so that the pump device 100 and controller device 200 can be worn in the user's pocket or in another portion of the user's clothing. In some circumstances, the user may desire to wear the pump assembly 15 in a more discrete manner. Accordingly, the user can pass the tube 147 from the pocket, under the user's clothing, and to the infusion site where the adhesive patch can be positioned. As such, the pump assembly 15 can be used to deliver medicine to the tissues or vasculature of the user in a portable, concealable, and discrete manner.

In some cases, the pump assembly 15 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these cases, the cap device 130 can have a configuration in which medicine passes directly from the cap device 130 into an infusion set 146 that is penetrated into the user's skin. In some examples, the user can temporarily detach the controller device 200 (while the pump device 100 remains adhered to the skin) so as to view and interact with the user interface 220.

Referring now to FIG. 1B, the pump device 100 in this example includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (e.g., including a battery powered actuator, a gear system, a drive rod, and other items that are not shown in FIG. 5) that advances a plunger 125 in the fluid cartridge 120 so as to dispense fluid therefrom. In this example, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 15 can provide enhanced user safety as a new pump device (and drive system therein) is employed with each new fluid cartridge. Additional and/or alternative implementations of the controller device 200 are also possible, including magnetic drive turbine (MDT) monolithic architecture pumps and/or omnipods.

The pump assembly 15 can be a medical infusion pump assembly that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Exenatide (BYETTA, BYDUREON) and liraglutide (VICTOZA)SYMLIN, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some cases, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some cases, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 1B, the controller device 200 can be removably attached to the pump device 100 so that the two components are mechanically mounted to one another in a fixed relationship. In some cases, such a mechanical mounting can also form an electrical connection between the removable controller device 200 and the pump device 100 (for example, at electrical connector 118 of the pump device 100). For example, the controller device 200 can be in electrical communication with a portion of the drive system (show shown) of the pump device 100. In some cases, the pump device 100 can include a drive system that causes controlled dispensation of the medicine or other fluid from the cartridge 120. In some cases, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the housing structure 110. Thus, when the pump device 100 and the controller device 200 are mechanically attached and thereby electrically connected, the controller device 200 communicates electronic control signals via a hardwire-connection (e.g., electrical contacts along connector 118 or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

Cap device 130 of the pump device 100 can be configured to mate with an infusion set 146. In general, the infusion set 146 can be a tubing system that connects the pump assembly 15 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 5) of the fluid cartridge 120 and the tube 147 of the infusion set 146.

Referring now to FIG. 1C, the controller device 200 (shown in an exploded view) houses a number of components that can be reused with a series of successive pump devices 100. In particular, the controller device 200 can include control circuitry 240 and a rechargeable battery pack 245, each arranged in the controller housing 210. The rechargeable battery pack 245 may provide electrical energy to components of the control circuitry 240, other components of the controller device (e.g., the display device 222 and other user interface components, sensors, or the like), or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. At least one memory device 242 of the control circuitry may be configured to store a number of user-specific dosage parameters. Various user-specific dosage parameters can be automatically determined and/or updated by control operations implemented by the control circuitry 240 of the controller device 200. Additionally, the control circuitry 240 can cause the controller device 200 to periodically communicate the user-specific dosage parameters to the mobile computing device 60 for future use during operations by the mobile computing device 60 or for subsequent communication to cloud-based computer network.

In some cases, the control circuitry 240 can receive input data or other information from the mobile computing device 60 (e.g., via user input at the mobile computing device 60) and thereby cause the controller device 200 to output information to the mobile computing device 60 for display on the screen of the mobile computing device 60, such as settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The control circuitry 240 can be programmable to cause the control circuitry 240 to change any one of a number of settings or modes of operation for the insulin delivery system 10. In some cases, the control circuitry 240 can include a cable connector (e.g., a USB connection port or another data cable port) that is accessible on an external portion of the controller housing 210. As such, a cable can be connected to the control circuitry 240 to upload or download data or program settings to the control circuitry.

A number of implementations have been described. Nevertheless, it will be understood that various modifications may be made without departing from the spirit and scope of the invention. Accordingly, other implementations are within the scope of the following claims.

What is claimed is:

1. A medical infusion pump system, comprising:
    a portable housing defining a space to receive a supply of insulin;
    a pump drive system to dispense insulin from the portable housing when the supply of insulin is received in the space;
    control circuitry that electrically communicates with the pump drive system to control dispensation of the insulin from the portable housing when the supply of insulin is received in the space;
    a blood glucose detection device comprising at least one of a continuous glucose monitor or a blood glucose meter;
    a user interface device including a display screen and being configured to receive user input and present one or more outputs on the display screen based on information received from the blood glucose detection device, the user interface device being in communication with the control circuitry and providing a graphic user interface on the display screen that includes:
        a first chart depicting a series of blood glucose values received from the blood glucose detection device aligned over a first axis to reflect the times that the blood glucose values were measured by the blood glucose detection device;
        a second chart depicting a series of insulin bolus amounts administered by the pump drive system aligned over a second axis to reflect the times that the insulin bolus amounts were administered; and
        a current time line that passes through the first axis of the first chart and the second axis of the second chart to identify a current time with respect to the first and second charts;
        wherein the first chart further depicts a projection of future blood glucose values on a right side of the current time line; and
        wherein the first axis of the first chart and the second axis of the second chart are time-aligned.

2. The medical infusion pump system of claim 1, wherein the user interface device comprises a mobile computing device in wireless communication with the control circuitry.

3. The medical infusion pump system of claim 2, wherein the mobile computing device is in direct wireless communication with the blood glucose detection device.

4. The medical infusion pump system of claim 2, wherein the mobile computing device is in indirect wireless communication with the blood glucose detection device via the control circuitry.

5. The medical infusion pump system of claim 1, further comprising a second blood glucose detection device;
    wherein the blood glucose detection device comprises a continuous glucose monitor;
    wherein the second blood glucose detection device comprises a blood glucose meter; and
    wherein the first chart depicts a series of blood glucose values received from the continuous glucose monitor aligned over the first axis to reflect the times that the blood glucose values were measured by the continuous glucose monitor, and a series of blood glucose values received from the blood glucose meter aligned over the first axis to reflect the times that the blood glucose values were measured by the blood glucose meter.

6. The medical infusion pump system of claim 5, wherein the blood glucose values received from the continuous glucose monitor are depicted using a first symbol and the blood glucose values received from the blood glucose meter are depicted using a second symbol, the second symbol being larger than the first symbol.

7. The medical infusion pump system of claim 1, wherein the graphic user interface further includes:
    a third chart depicting a step graph of a plurality of basal insulin delivery rates reflecting rates of basil insulin delivery by the pump drive system aligned over a third axis to reflect times of the basal insulin delivery rates;
    wherein the third axis of the third chart is time-aligned with the first axis of the first chart and the second axis of the second chart.

8. The medical infusion pump system of claim 7, wherein the
    current time line passes through the third axis of the third chart to identify the current time with respect to the first, second, and third charts; and
    wherein the third chart further depicts a projected basil insulin delivery rate on the right side of the current time line.

9. The medical infusion pump system of claim 1, wherein the graphic user interface further includes a projected blood glucose value and a time for the projected blood glucose value, wherein the time for the projected blood glucose value is between 15 minutes and 4 hours after a most recent blood glucose measurement.

10. The medical infusion pump system of claim 1, wherein the graphic user interface further includes an arrow indicating a projected profile of how blood glucose values are expected to change over a future time period, the time period being a length of time between 30 minutes and 4 hours.

11. A method of operating a medical infusion pump system, the method comprising:
    receiving, at a mobile computing device, a plurality of blood glucose measurement values and corresponding measurement times for each of the blood glucose measurement values from a blood glucose detection device, the blood glucose detection device comprising at least one of a continuous glucose monitor or a blood glucose meter;

receiving, at the mobile computing device, information indicating a plurality of insulin bolus dosage values for insulin bolus dosages administered by a pump device of the medical infusion pump system and corresponding bolus administration times for each of the insulin bolus dosage values;

displaying, by the mobile computing device, a first graphic user interface having a first selectable input;

receiving, by the mobile computing device, user selection of the first selectable input of the first graphic user interface;

displaying, by the mobile computing device and in response to receiving the selection of the first selectable input, a second graphic user interface, the second graphic user interface including:
  a first chart depicting the plurality of blood glucose values received from the blood glucose detection device plotted over a first time axis according to the corresponding measurement times for each of the blood glucose measurement values;
  a second chart depicting the plurality of insulin bolus dosage values for insulin bolus dosages administered by the pump device plotted over a second time axis according to the corresponding bolus administration times for each of the insulin bolus dosage values; and
  a current time line that passes through the first axis of the first chart and the second axis of the second chart to identify a current time with respect to the first and second charts;
  wherein the first chart further depicts a projection of future blood glucose values on a right side of the current time line; and
  wherein the first time axis of the first chart and the second time axis of the second chart are time-aligned.

12. The method of claim 11, wherein the mobile computing device is in wireless communication with control circuitry in electrical communication with a pump drive system of the pump device to control dispensation of medicine from the pump device and wherein the bolus dosages administered by the pump device are administered in response to control signals communicated from the mobile computing device to the control circuitry.

13. The method of claim 11, wherein receiving the plurality of blood glucose measurement values comprises receiving a first plurality of blood glucose measurement values from a continuous glucose monitor and receiving a second plurality of blood glucose measurements from a blood glucose meter; and
  wherein the first chart depicts the first plurality of blood glucose measurement values received from the continuous glucose monitor aligned over the first time axis to reflect the times that each of the first plurality of blood glucose measurement values were measured by the continuous glucose monitor, and the second plurality of blood glucose measurement values received from the blood glucose meter aligned over the first time axis to reflect the times that each of the second plurality of blood glucose measurement values were measured by the blood glucose meter.

14. The method of claim 13, wherein the blood glucose measurement values received from the continuous glucose monitor are depicted using a first symbol and the blood glucose measurement values received from the blood glucose meter are depicted using a second symbol, the second symbol being larger than the first symbol.

15. The method of claim 11, wherein the second graphic user interface further includes:
  a third chart depicting a step graph of a plurality of basal insulin delivery rates reflecting rates of basil insulin delivery by the pump device aligned over a third time axis to reflect times of the basal insulin delivery rates;
  wherein the third time axis of the third chart is time-aligned with the first time axis of the first chart and the second time axis of the second chart.

16. The method of claim 15, wherein the
  current time line passes through the third axis of the third chart to identify the current time with respect to the first, second, and third charts; and
  wherein the third chart further depicts a projected basil insulin delivery rate on the right side of the current time line.

17. The method of claim 11, wherein the second graphic user interface further includes a projected blood glucose value and a time for the projected blood glucose value, wherein the time for the projected blood glucose value is between 15 minutes and 4 hours after a most recent blood glucose measurement.

18. The method of claim 11, wherein the second graphic user interface further includes an arrow indicating a projected profile of how blood glucose values are expected to change over a future time period, the time period being a length of time between 30 minutes and 4 hours.

19. The method of claim 11, wherein the first chart depicts a series of blood glucose values received from a continuous glucose monitor aligned over the first axis to reflect the times that the blood glucose values were measured by the continuous glucose monitor, and a series of blood glucose values received from a blood glucose meter aligned over the first axis to reflect the times that the blood glucose values were measured by the blood glucose meter.

20. The method of claim 19, wherein the blood glucose values received from the continuous glucose monitor are depicted using a first symbol and the blood glucose values received from the blood glucose meter are depicted using a second symbol, the second symbol being larger than the first symbol.

* * * * *